(12) United States Patent
Rowe

(10) Patent No.: US 6,303,572 B1
(45) Date of Patent: Oct. 16, 2001

(54) CONTROL OF ACIDIC GUT SYNDROME

(75) Inventor: James Baber Rowe, Armidale (AU)

(73) Assignee: University of New England, of Armidale (AU)

( * ) Notice: Subject to any disclaimer, the term of this patent is extended or adjusted under 35 U.S.C. 154(b) by 0 days.

(21) Appl. No.: 09/446,801

(22) PCT Filed: Jun. 26, 1998

(86) PCT No.: PCT/AU98/00495

§ 371 Date: Feb. 10, 2000

§ 102(e) Date: Feb. 10, 2000

(87) PCT Pub. No.: WO99/00136

PCT Pub. Date: Jan. 7, 1999

(30) Foreign Application Priority Data

Jun. 27, 1997 (AU) ................................................... PO7582

(51) Int. Cl.⁷ ............................ A61K 38/16; A61K 38/00; A61K 31/70; A61K 31/715; A61K 31/65

(52) U.S. Cl. ........................ 514/6; 514/8; 514/9; 514/31; 514/37; 514/54; 514/152; 514/200; 514/311; 514/866; 514/903

(58) Field of Search ............................... 514/8, 9, 29, 37, 514/200, 152, 311, 54, 31, 6, 866, 903

(56) References Cited

FOREIGN PATENT DOCUMENTS

32284/89 10/1989 (AU).
43245/96 7/1996 (AU).

OTHER PUBLICATIONS

Nagaraja et al., (1981) *Journal of Animal Science*, vol. 53, pp. 206–216.

Muir et al., (1980) *Journal of Animal Science*, vol. 50, pp. 547–553.

Kung and Hession. "Preventing In Vitro Lactate Accumulation in Ruminal Fermentations by Inoculation with *Megasphaera esdenii*." Department of Animal Science & Agricultural Biochemistry, University of Delaware, Newark 19717–1303, pp. 250–256.

*Primary Examiner*—Kevin E. Weddington
(74) *Attorney, Agent, or Firm*—McDonnell Boehnen Hulbert & Berghoff

(57) ABSTRACT

According to the present invention there is provided a method for the treatment or prophylaxis of acidic gut syndrome resulting from the accumulation of acid and production of endotoxin in the gastrointestinal tract of a human or an animal, said accumulation resulting from the fermentation of carbohydrate in the gastrointestinal tract of said human or animal, wherein said method comprises administering to said human or animal an effective amount of an active agent capable of preventing or controlling acid and endotoxin accumulation in the gastrointestinal tract.

15 Claims, 10 Drawing Sheets

CONTROL OF ACIDIC GUT SYNDROME

TECHNICAL FIELD

This invention relates to the treatment or prophylaxis of conditions resulting from acidic gut syndrome in humans or an animals, wherein acidic gut syndrome results from the fermentation of carbohydrate in the gastrointestinal tract of the human or animal. The problems associated with acidic gut syndrome, and overcome with treatment, include: predisposition to ulceration of the gastrointestinal tract; ulceration of the stomach; immune conditions associated with localised inflammation of the gut including irritable bowel disorder, crohn's disease, appendicitis, colitis and reduced feed intake, responsible for cachexia and low efficiency in production feeding systems; dermatitis; arthritis; rheumatoid arthritis; osteoarthritis; respiratory tract disorders, including asthma and predisposition to bleeding in lungs following strenuous exercise; predisposition to microbial and helminth infections of the gut, and infection of the mammary gland, including mastitis; immune disorders causing predisposition to infection by bacteria, fungi or protozoa; cystic fibrosis and certain cancers; effects on the pancreas, kidneys, thyroid and other organs and conditions of the endocrine system, including diabetes; homeostasis disorders, including blood pH, mineral and electrolyte imbalances, such as osteoporosis and hypertension; immune disorders, including multiple sclerosis, amyotrophic lateral sclerosis, chronic fatigue syndrome, myasthenia gravis, Alzheimer's disease, impaired reproductive performance; dental caries; viral infections, including herpes; exacerbation of heat stress; and impaired hair and wool growth.

BACKGROUND ART

Carbohydrates are digested through enzymic breakdown and absorption of simple sugars or through microbial fermentation and absorption of short chain volatile fatty acids. A condition known as lactic acidosis (D-lactic acidosis, fermentative acidosis or carbohydrate overload) is widely recognised in ruminants and horses. This condition is responsible for deaths in ruminant livestock feeding, and in horses is associated with the development of laminitis (Garner et al. 1987, Rowe et al. 1994) and abnormal behaviour (Johnson et al. 1998). Lactic acidosis can also lead to diarrhoea, infections in the hind gut and skin disorders. The pathogenesis of lactic acidosis is described as a good example of metabolic acidosis in which considerable amounts of lactic acid are absorbed through the wall of the gut (Blood et al. 1983). D-lactic acid is more slowly metabolised than L-lactic acid and therefore accumulates in the tissues where it causes severe D-lactic acidosis. These authors also suggest that endotoxins from gram-negative bacteria in the gut may play a role in the pathogenesis of lactic acidosis (Blood et al. 1983), as it is possible that these endotoxins may be absorbed as a result of severe structural damage to the gut epithelium which occurs during this condition (Krueger et al. 1986).

The present invention describes a new condition, described as acidic gut syndrome, which differs significantly from lactic acidosis in that it does not involve metabolic acidosis, resulting from acid absorption from the gastrointestinal tract, as a factor in its pathogenesis. Acidic gut syndrome depends entirely on acidity within the gut and the adverse toxic effects mediated through the direct effect of acid on the gut wall and through effects of acidity on microbes within the gut. Acidic gut syndrome has a range of secondary consequences which develop from the primary effects of acidity within the gut. These secondary effects occur both locally and systemically. Locally, the effects are through the action of acidity and bacterial endotoxins (produced for example, through the death of gram negative bacteria under acidic conditions) on the gut wall itself. Systemically the effects are considered to be mediated via the immune system and a range of cytokine and related factors. Furthermore, it is thought that the gut wall and gut associated lymphoid tissue play a role in acidic gut syndrome through mediating the effects of toxins or other factors, and releasing systemically active hormones and/or agents of the immune system.

There are a number of immune system diseases, of a chronic and/or acute nature, which are of unknown aetiology. The common factor appears to be the involvement of various cytokines and other mediators of the immune system. Because the aetiology of these immune-related conditions has not been understood they have generally been considered to be non-specific immune diseases. Examples of immune diseases considered in this category are forms of arthritis, including rheumatoid arthritis, forms of respiratory disease and susceptibility to respiratory problems such as asthma, reduced enzyme production by the pancreas leading to some forms of diabetes, damage to kidneys resulting in mineral imbalances and hypertension, effects on the brain which can lead to secondary hormone imbalances with respect to control of temperature regulation, reproductive functions and other key aspects of metabolic control. The effects mediated via the immune system (cytokine and possibly other activities) can also cause inflammation and damage membranes in organs and tissues remote from the sites of bacterial activity within the gut. Organs and tissues affected in this way can include the lung (which subsequently increases the risk of respiratory tract infection), the stomach (which increases the risk of ulcer development), the kidneys (affecting mineral retention and hypertension). There can also be local areas of non-specific inflammation such as can occur in the gut or around the teeth. These conditions are considered to result from a minor build up of acidity within the gut and the release of endotoxins associated with the death of gram negative bacteria as acidity increases and gram positive bacteria predominate.

The slight increases in levels of both acidity and endotoxin within the gut associated with acidic gut syndrome, effect the host via a subtle increase in the immune challenge. The barrier between the host and the gastrointestinal microflora is extremely important in preventing infection and/or toxaemia. The present invention describes how the immune challenge to the host from the gut is not constant and can be increased in response to levels of acid in the gut which have until now been considered within normal limits and of no biological consequence. Increased acidity and changes in gut bacteria, particularly in relation to endotoxin production, produces a challenge which may not necessarily lead to an immediately detectable disease condition or a dramatic immunological response in the animal. It does however pose a sufficient challenge to the immune system of the animal or human to cause measurable responses (for example raised levels of tumour necrosis factor (TNF), T-cells, monocytes, interferon and cytokines, including interleukin-1, -6 and -8). Because these changes to the immune system are small and in themselves do not cause symptoms or signs of disease they have not previously been linked to changes in the diet or digestive process. Slightly elevated levels of cytokines and or TNF tend to be transitory and have previously been regarded as normal variation between individuals or non-specific immune conditions, and for these reasons have not been studied systematically with a view to determining the importance of diet and microbial activity within the gut. There has therefore been no previous suggestion that diet, fermentation within the gut, and subsequent acid accumulation and endotoxin production in the gut (acidic gut syndrome), are the primary causes of serious chronic and/or sporadic disease conditions of previously unknown origin.

There is a dense and diverse population of bacteria which inhabit the gastro-intestinal tract of man and animals. The concentration of these bacteria occurs naturally in those parts of the tract where the conditions of pH are close to neutral (around pH 6.5 to 7.5) and where fermentable substrate is available for fermentation. The bacteria in the gut poses a potential risk to the animal in terms of infection from the gut or through the absorption of microbial toxins.

The medical and nutritional literature contains information on various approaches used to manage the microbial population within the gut of humans. Two of these are summarised below.

1. The creation of a population of lactic acid producing bacteria in the gut through inoculation with probiotics such as cultures of Lactobacilli and other lactic acid producing bacteria, in the form of yoghurt cultures or specifically cultured bacteria preparations. The hypothesis behind this practice is that the lactic acid production may exclude other, more pathogenic, bacteria from the gut.

2. Consumption of increased amounts of soluble fibre which consists of indigestible (but fermentable) sources of starch (resistant starch) and oligosaccharides in order to provide substrates for fermentation in the hind gut. The aim of this practice is to increase the production of butyric acid, which has been shown, in vitro, to enhance the metabolism of the gut epithelium and reduce the risk of colonic cancer.

It is clear that these practices, now widely recommended by dietitians and medical practitioners, are likely to increase the amount of fermentable acid production and, specifically, the amount of lactic acid and are therefore likely to promote acidic gut syndrome.

The present invention describes how the elevated activity of the immune system, as a result of acidic gut syndrome, is sufficient to initiate, or predispose, the host to a range of secondary conditions including immune diseases, inflammation, infection and damage to membranes, by cytokine, or other immune system activity, and provides a method for the treatment or prophylaxis of acidic gut syndrome.

DISCLOSURE OF THE INVENTION

According to a first embodiment of this invention, there is provided a method for the treatment or prophylaxis of acidic gut syndrome resulting from the accumulation of acid and production of endotoxin in the gastrointestinal tract of a human or an animal, said accumulation resulting from the fermentation of carbohydrate in the gastrointestinal tract of said human or animal, wherein said method comprises administering to said human or animal an effective amount of an active agent capable of preventing or controlling acid and endotoxin accumulation in the gastrointestinal tract.

Typically, the active agent may be selected from the group consisting of: antibiotics, enzyme preparations, clay preparations, compounds which slow the digesta flow rate and probiotic preparations.

A suitable active agent of the first embodiment of the invention may include an antibiotic whose action is to control acid producing gram-positive bacteria.

Typically, the antibiotic may be selected from the group consisting of: a glycopeptide antibiotic, a glycolipid antibiotic, a staphylomycin antibiotic, a polypeptide antibiotic, a macrolide antibiotic, a sulphur-containing peptide antibiotic, a lincosamide antibiotic, tiamulin, a nitrofuran antibiotic, a tetracycline antibiotic, a penicillin antibiotic, a polythiazole antibiotic, an ionophore antibiotic, a cephalosporin antibiotic, a sulphonamide antibiotic, an aminoglycoside antibiotic, a quinalone antibiotic, streptogramin antibiotic, and any other antibiotic active against gram-positive bacteria responsible for the production of acid in the gastrointestinal tract.

Even more typically, the antibiotics active against gram-positive bacteria may be selected from the group consisting of:- glycopeptide antibiotics, more typically, avoparcin, teicoplanin or vancomycin; glycolipid antibiotics, more typically flavomycin (bambermycin); staphylomycin antibiotics, more typically virginiamycin; polypeptide antibiotics, more typically bacitracin zinc, bacitracin methylene disalicylate, virginiamycin S or polymixins (B & E); macrolide antibiotics, more typically tylosin, spiramycin, virginiamycin M, josamycin, spectinomycin or erythromycin; or sulfur-containing peptide antibiotics, more typically thiopeptone, thiopeptin, sulfomycin, thiostrepton, sporangiomycin, siomycin or taitomycin; lincosamide antibiotics, more typically lincomycin or clindamycin; or tiamulin; or nitrofuran antibiotics, more typically nitrofurantoin, nitrofurazone or furazolidone; tetracycline antibiotics, more typically chlortetracycline or oxytetracycline; penicillin antibiotics, more typically penicillinase-resistant penicillins, such as oxacillin or methicillin, penicillin V or ampicillin; polythiazole antibiotics, more typically nosiheptide; or ionophore antibiotics, more typically lasalocid, tetronasin, naracin or salinomycin; or ardacin, novobiocin sodium, bottromycin tartrate; streptogramin antibiotics, more typically, quinupristin/dalfopristin (RP 59500; Synercid) or streptogramin combinations [quinupristin/dalfopristin (RP 59500; Synercid)], everninomycin derivatives (SCH 27899), oxazolidinones (U-100572, U-100766); fluoroquinolone antibiotics, more typically, ciprofloxacin, ofloxacin, clinafloxacin, DU 6859a, grepafloxacin, levofloxacin, sparfloxacin or trovafloxacin; beta-lactam antibiotics; nitrovin (payzone), enramycin, mupiricin, margainin antibiotics, chloramphenicols and related compounds, including florphenicol, and any combination thereof.

A suitable active agent of the first embodiment of the invention may include an exogenous enzyme preparation designed to reduce the passage of fermentable carbohydrate to the hind gut through improving the digestion and absorption in the intestine of starches, disaccharides, oligosaccharides, non-starch polysaccharides, protein starch complexes and any polysaccharide which is incompletely digested in the intestine, but which is readily fermentable in the hind gut.

Typically preferred enzymes for the break down of non-starch polysaccharides and starches include the following: glyconases including: amylase, maltase, invertase, α-glucosidases, emulsin, and amyloglucosidase; glucanases β-glucanase, xylanase; enzymes which break down galactosides of the raffinosse series and other α-galactosides including α-galactosidase, enzymes which break down the proteins forming part of the matrix surrounding starches, sugars and non-starch carbohydrates in plant material, including: pepsin, trypsin, trypsinogen, chymotrypsin and natural and synthetic proteolytic enzymes of chemical or microbial origin, enzymes which depolymerise non-starch polysaccharides including: arabinoxylans and β-glucans, and enzymes active in the break down of cellulose, including: cellulase, enzymes active in the break down of colloidal polysaccharides, pectic substances, which include: galactouronans, galactan and arabinans, as well as the neutral polysaccharides such as xyloglucans and galactomannans and other non-starch polysaccharides such as: rhamnogalactouronan with arabinose and galactose, arabinogalactan, glucan, xyloglucan, galactouronan with arabinose and uronan with arabinose. These enzymes can be used individually or in combination.

A suitable active agent of the first embodiment of the invention may include a clay preparation which reduces the rate of fermentation and binds specific ions in a way which reduces the adverse effects of rapid fermentation of starch and other soluble carbohydrates in the gastrointestinal tract.

Typically, preferred clays for reducing the rate of fermentation and the osmotic effects of rapid fermentation within the gut include: kaolinite, bentonite, montmorrilonite, illite, clinoliptolite, heulandite, palygorsite, saponite, smectite, chrysotile, lizardite, talc, pyrophyllite, vermiculite, beidellite, halloysite or zeolite types of clay, and these can be activated by a wide range of ions including sodium, calcium, potassium and mixtures of these and other ions. These clays can be used individually or in combination.

A suitable active agent of the first embodiment of the invention may include a compound which slows digesta flow rate, thereby increasing intestinal digestion and absorption and reducing the amount of fermentable substrate passing to the hind gut.

Generally, preferred agents to slow the flow of digeseta include biologically active peptides (BAP) in a form which will reach the duodenum, and are active in modulating the activity of the digestive tract, gastric emptying and the rate of passage through the intestine. More typically, these biologically active peptides include opioid peptides.

Whilst a range of proteins potentially produce opioid peptides on hydrolisation, the β-casomorphins, which can be derived from β-casein during β-casein digestion, are particularly active.

Even more typically, the biologically active peptides include cholecystokinin (CCK), the M1 fraction of virginiamycin and the analogue of virginiamycin fraction M1, compound L-156. These biologically active peptides can be used individually or in combination.

It has traditionally been assumed that the nutritional benefits of proteins are only related to the essential amino acids supplied to the animal during digestion and absorption. However through the supply of biologically active peptides and the production of naturally occurring opioid peptides, the rate of digesta passage is reduced and this results in more efficient intestinal digestion and less fermentable substrate passing to the hind gut which can contribute to acidic gut syndrome.

Practical methods of supplying biologically active opioid peptides is through dietary supplementation with proteins such as casein and blood meal. For ruminant animals the best results are obtained through protection of the protein against rumen degradation by polymer coating technology, slow-release capsules, or through formaldehyde treatment.

A suitable active agent of the first embodiment of the invention may include a probiotic preparation which reduces lactic acid accumulation by: formation of alternative end products of fermentation; production of volatile fatty acids rather than lactic acid during carbohydrate fermentation; through increased utilisation of lactic acid; or through the conversion of lactic acid to volatile fatty acids which can be absorbed from the gut, thereby reducing acidity in the gut.

Typically, preferred probiotic preparations include bacteria which ferment starch and sugars to end products other than lactic acid, (ie volatile fatty acids).

More typically, the probiotic preparations may include bacteria selected from the group consisting of: Succinomonas, Butyrivibrio, Bacteroides and Succinivibrio. These bacteria can be used individually or in combination.

Typically, preferred probiotic preparations include bacteria capable of utilising lactic acid, and converting lactic acid to volatile fatty acids and other end products.

More typically, the probiotic preparations may include anaerobic bacteria.

Even more typically, the probiotic preparations may include bacteria selected from the group consisting of: Megasphera, Veillenolla, Selenomonas, Propionibacterium, Anaerovibrio and Peptococcus. These bacteria can be used individually or in combination.

Typically, preferred probiotic preparations include yeast and mycelial preparations capable of utilising lactic acid, and converting lactic acid to volatile fatty acids and other end products.

More typically, the probiotic preparations may include yeast and mycelial preparations such as Yea Sacc.

Typically, at least any two of the above sample microrganisms of the probiotic preparation may be used in combination in the probiotic preparation.

According to a further aspect of the invention, the active agent may include a combination of at least two of: an antibiotic, an exogenous enzyme preparation, a clay, a compound which slows digesta flow rate, or a probiotic preparation.

Compositions for administration of the active agent in the method of the invention may be prepared by means known in the art for the preparation of compositions (such as in the art of veterinary and pharmaceutical compositions) including blending, grinding, homogenising, suspending, dissolving, emulsifying, dispersing and where appropriate, mixing of the active agent, together with selected excipients, diluents, carriers and adjuvants.

For oral administration, the pharmaceutical or veterinary composition may be in the form of tablets, lozenges, pills, troches, capsules, elixirs, powders, including lyophilised powders, solutions, granules, suspensions, emulsions, syrups and tinctures. Slow-release, or delayed-release, forms may also be prepared, for example in the form of coated particles, multi-layer tablets or microgranules.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further include dispersing agents and/or suspending agents. Suitable suspending agents include sodium carboxymethylcellulose, methylcellulose, hydroxypropylmethyl-cellulose, polyvinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further include one or more emulsifying agents. Suitable emulsifying agents include dispersing agents as exemplified above or natural gums such as guar gum, gum acacia or gum tragacanth.

In another form the invention resides in a method of treating animals or humans which comprises delivering to the alimentary canal a quantity of an active agent of the form described above.

Typically the active agent can be administered by binding it to fibrous materials which pass undigested into the caecum, colon or other part of the hind gut or it can be incorporated into specially formulated feeds and foods or administered in the form of premixes, pastes, gels, gums, pellets or cubes. In one particular form of the invention, administration of the active agent to human or animal subjects is in the form of digestible capsules which release the active material into the stomach, intestine or hindgut.

The active agents may be administered with the carbohydrate feed. The active agent can be mixed with the feed during preparation, added to the feed before consumption or oral administration or sprinkled on top of the food before it is consumed. In one particular form of the invention, in the administration of the active agent to human subjects, the active agent can be mixed with herbs and spices coating starch based foods such as biscuits and snack foods. Further, the active agent can be included in pelleted feeds for animals and/or in loose mixes.

Typically, the active agent may be administered directly into the buccal cavity.

Typically, administration of the active agent to human subjects may be in the form of toothpaste which releases the active agent into the buccal cavity.

Typically, the active agent may be administered to the human or animal subjects via targeted delivery to the hind gut using enteric coated delivery systems to ensure specific activity of the active agent in the terminal ileum, colon and/or caecum.

Typically, targeted delivery to different parts of the gastrointestinal system is achieved by multiple coatings of the active agent with materials sensitive to pH and/or enzyme activity, and/or microbial fermentation and/or time-dependent solubility.

Typically, a method of treating animals in accordance with the present invention may include delivering to the alimentary canal a quantity of between 1 and 10% of total feed material of an active agent of the form described above, and 90–99% feed material wherein the feed material includes between 1 and 10% of fibrous material. Typically the fibrous material may be lucerne chaff.

The administered dose of the antibiotic can vary and will depend on several factors, such as the condition, age and size of the human or animal patient, as well as the nature of the lactic acid producing gram-positive bacteria. Dosages will typically range from between 0.01 and 5 mg per kg of bodyweight. More typically dosages will range from between 0.02 and 2.0 mg per kg of bodyweight. More typically dosages will range from between 0.05 and 1.0 mg per kg of bodyweight. Even more typically dosages will range from between 0.1 and 0.5 mg per kg of bodyweight. Yet even more typically, the antibiotic is administered to the human or animal at a rate of 0.4 mg per kg of bodyweight.

Typically, the antibiotic is administered at a rate of between 1 and 100 mg per kg of dry weight of food. More typically, the antibiotic is administered at a rate of between 1 and 75 mg per kg of dry weight of food. Even more typically, the antibiotic is administered at a rate of between 1 and 50 mg per kg of dry weight of food. Yet even more typically, the antibiotic is administered at a rate of between 5 and 40 mg per kg of dry weight of food.

As above, the administered dose of the enzyme preparation can vary and will depend on several factors, such as the condition, age and size of the human or animal patient, as well as the nature of the carbohydrate. Dosages will typically range from between 0.01 and 50 g/kg food dry matter. Typically, the enzyme is administered at a rate of between 0.1 and 3 g per kg of dry weight of food. More typically, the enzyme is administered at a rate of between 1 g per kg of dry weight of food.

Similarly, the administered dose of the clay preparation can vary and will depend on several factors, such as the condition, age and size of the human or animal patient, as well as the nature of the carbohydrate. Dosages will typically range from between 0.5 and 100 g/kg, food dry matter. Typically, the clay is administered at a rate of between 1 and 50 g per kg of dry weight of food. More typically, the clay is administered at a rate of between 10 and 20 g per kg of dry weight of food.

Typically, the administered dose of the probiotic preparation can vary between $10^6$ and $10^{12}$ bacteria per kg of body weight. More typically, dose of the probiotic preparation can vary between $10^8$ and $10^{10}$ per kg of body weight.

According to another form of the invention, the active agents can be used together.

According to another aspect of the invention, the formulation of the active agent ensures that it is administered in a palatable form to the animal or human and in a form which retains activity and is properly mixed in the appropriate compartment(s) of the gastrointestinal tract.

Generally, the active agent is administered regularly throughout the period the animal or human is subjected to a high carbohydrate diet or to sugars or other fermentable compounds which are not efficiently absorbed prior or reaching the large intestine, colon and caecum.

More typically, the active agent is administered 1–3 times daily. Even more typically, the active agent is administered once daily or can be included in human food and animal feeds. They can be fed as powders or suspended in water, included in pellets as well as being fed in premixes.

More typically the active agent is mixed with the food, or is added to feeds which contain starch or sugars which may produce an acidic pattern of fermentation in the gastrointestinal tract.

A suitable treatment may include the administration of a single dose or multiple doses. Usually, the treatment will consist of administering one dose daily of the active agent for a period sufficient to control the accumulation of acid by fermentation of the carbohydrate in the gastrointestinal tract. Dosing may continue while sources of carbohydrate known to cause problems of acidic fermentation in the gastrointestinal tract are included in the diet.

More typically the active agent may be administered in a single dose immediately before consuming meals containing sources of carbohydrate which are poorly digested and rapidly fermented.

More typically, the active agent is administered for one day prior to and daily during the consumption of excessive quantities of food stuffs containing readily fermentable carbohydrates.

Typically, the active agent is administered orally.

According to a second embodiment of the invention, there is provided a method for the treatment or prophylaxis of acidic gut syndrome resulting from the accumulation of acid and production of endotoxin in the gastrointestinal tract of a human or an animal, said accumulation resulting from the fermentation of carbohydrate in the gastrointestinal tract of said human or animal, which method comprises immunising said human or animal against the microorganisms responsible for the fermentation of carbohydrate in the gastrointestinal tract of said human or animal.

Typically, the human or animal is immunised against bacteria which produce lactic acid in the gut and therefore primary agents in the development of acidic gut syndrome.

Typically, bacteria against which the human or animal is immunised include: Aerococcus, Alloiococcus, Carnobacterium, Enterococcus, Lactobacillus, Lactococcus, Leuconostoc, Pediococcu, Streptococcu and Tetragenacoccus among others.

More typically, bacteria against which the human or animal is immunised include: Lactobacillus spp. and *Streptococcus bovis* type.

Even more typically, bacteria against which the human or animal is immunised is *Streptococcus bovis* (Sb-5).

For example, immunisation may be achieved by intramuscular or sub-cutaneous injection of for example, a mixture of Lactobacillus spp. and *Streptococcus bovis*, or either bacteria administered individually, together with a suitable adjuvant, excipient, diluent and/or carrier.

Typically, the adjuvant may include Quil A, Dex and Alum, cytokines, among others, and be of a variety of types suitable for different host species.

Typically, numerous strains of Lactobacillus spp. and *Streptococcus bovis* are suitable, and can be cultured using carbohydrate-rich media from rumen contents, caecal digesta or faeces.

Typically, a priming dose is followed by regular boosters to maintain immunity.

Typically, the dosage rate for immunisation is between $1 \times 10^9$ and $1 \times 10^{11}$ bacterial cells per injection.

Typically, the dosage rates are approximately equivalent to between $1 \times 10^8$ to $1 \times 10^9$ bacterial cells per kg body weight.

More typically, the dosage rates are approximately equivalent to between $1 \times 10^8$ and $5 \times 10^8$ bacterial cells per kg body weight.

Even more typically, the dosage rates are approximately equivalent to $2.5 \times 10^8$ bacterial cells per kg body weight.

Typically, the dosage rate for immunisation of small animals, such as sheep, is between $5 \times 10^9$ and $5 \times 10^{10}$ bacterial cells per injection.

More typically, the dosage rate for immunisation of small animals, such as sheep, is approximately $1 \times 10^{10}$ bacterial cells per injection.

Typically, the dosage rate for immunisation of large animals, such as cattle and horses, is between $1 \times 10^{10}$ and $1 \times 10^{12}$ bacterial cells per injection.

More typically, the dosage rate for immunisation of large animals, such as cattle and horses, is approximately $1 \times 10^{11}$ bacterial cells per injection.

Typically, the injection volume for sheep is between 1 mL to 3 mL, and 2 to 7 mL for cattle and horses 3 to 5 mL.

More typically, the injection volume for sheep is between 1 mL to 2 mL, and 3 to 5 mL for cattle and horses.

The methods of the first or second embodiments of the invention are effective in the treatment or prophylaxis of the conditions associated with acidic gut syndrome.

The conditions associated with acidic gut syndrome, and treated by the methods of the first or second embodiments of the invention, include: predisposition to ulceration of the gastrointestinal tract; ulceration of the stomach; immune conditions associated with localised inflammation of the gut including irritable bowel disorder, crohn's disease, appendicitis, colitis and reduced feed intake, responsible for cachexia and low efficiency in production feeding systems.

The conditions associated with acidic gut syndrome, and treated by the methods of the first or second embodiments of the invention, even further include: dermatitis; arthritis; rheumatoid arthritis; osteoarthritis; respiratory tract disorders, including asthma and predisposition to bleeding in lungs following strenuous exercise.

The conditions associated with acidic gut syndrome, and treated by the methods of the first or second embodiments of the invention, still further include: predisposition to microbial and helminth infections of the gut, and infection of the mammary gland, including mastitis.

The conditions associated with acidic gut syndrome, and treated by the methods of the first or second embodiments of the invention, yet still further include: immune disorders causing predisposition to infection by bacteria, fungi or protozoa; cystic fibrosis and certain cancers.

The conditions associated with acidic gut syndrome, and treated by the methods of the first or second embodiments of the invention, yet still even further include: effects on the pancreas, kidneys, thyroid and other organs and conditions of the endocrine system, including diabetes; homeostasis disorders, including blood pH, mineral and electrolyte imbalances, such as osteoporosis and hypertension.

The conditions associated with acidic gut syndrome, and treated by the methods of the first or second embodiments of the invention, also include: immune disorders, including multiple sclerosis, amyotrophic lateral sclerosis, chronic fatigue syndrome, myasthenia gravis, Alzheimer's disease, impaired reproductive performance; dental caries; viral infections, including herpes; exacerbation of heat stress; and impaired hair and wool growth.

According to a third embodiment of the invention, there is also provided a method of diagnosing acidic gut syndrome.

Typically, the method for diagnosing acidic gut syndrome comprises determining the pH of the gastrointestinal tract of said human or animal.

More typically, the pH of the gastrointestinal tract may be determined through pH indicator solutions or devices added to the toilet bowl, or pH indicator solutions, or devices, used in conjunction with stool collections chambers.

Typically, the pH indicator solutions may involve pH sensitive colour reagents.

More typically, the pH indicator devices, used in conjunction with stool collections chambers, may involve paper strips.

Even more typically, the paper strips are litmus paper.

Yet even more typically, the litmus paper may be incorporated into toilet paper.

Typically, the acid which accumulates in the gastrointestinal tract includes: volatile fatty acids, and/or lactic acid.

Typically, the test for acidity may involve measurement of specific acids present in the faecal material, such as volatile fatty acids, and/or lactic acid.

Typically, acid measurement is performed using specific quantitative measurements, wherein such measurements may be made using chromatographic or spectroscopic techniques to measure individual acid concentrations.

Typically, the method for diagnosing acidic gut syndrome comprises determining the concentration of cytokines in the gastrointestinal tract, faeces and/or plasma of said human or animal.

Typically, the cytokine measured is selected from the group consisting of: tumour necrosis factor (TNF), interferon and interleukin.

Generally, the level of cytokine is measured via radioimmunoassay, ELISA or other molecular biological detection techniques.

Typically, the method for diagnosing acidic gut syndrome comprises determining the presence of bacterial endotoxins/lipopolysaccharides in the gastrointestinal tract of said human or animal.

The bacterial endotoxins/lipopolysaccharides may be detected through nucleic acid hybridisation and/or amplification.

Typically, hybridisation detection occurs via a nucleic acid probe specific for a bacterial endotoxin/lipopolysaccharide.

Typically, nucleic acid amplification may also provide a method of detection, and may occur via a pair of nucleic acid primers specific for a bacterial endotoxin/lipopolysaccharide.

More typically, amplification may be carried out using the ligase chain reaction (LCR).

Even more typically, amplification may be carried out using the polymerase chain reaction (PCR).

The bacterial endotoxins/lipopolysaccharides may be detected via an antibody detection system.

Typically, the detection system may involve the use of at least one polyclonal antibody.

More typically, the detection system may involve the use of at least one monoclonal antibody.

Typically, bacterial endotoxin/lipopolysaccharide may be measured using the limulus amoebocyte lysate system.

This shows that unless lactic acid is present the pH does not fall below 5.5.

Figure 1:
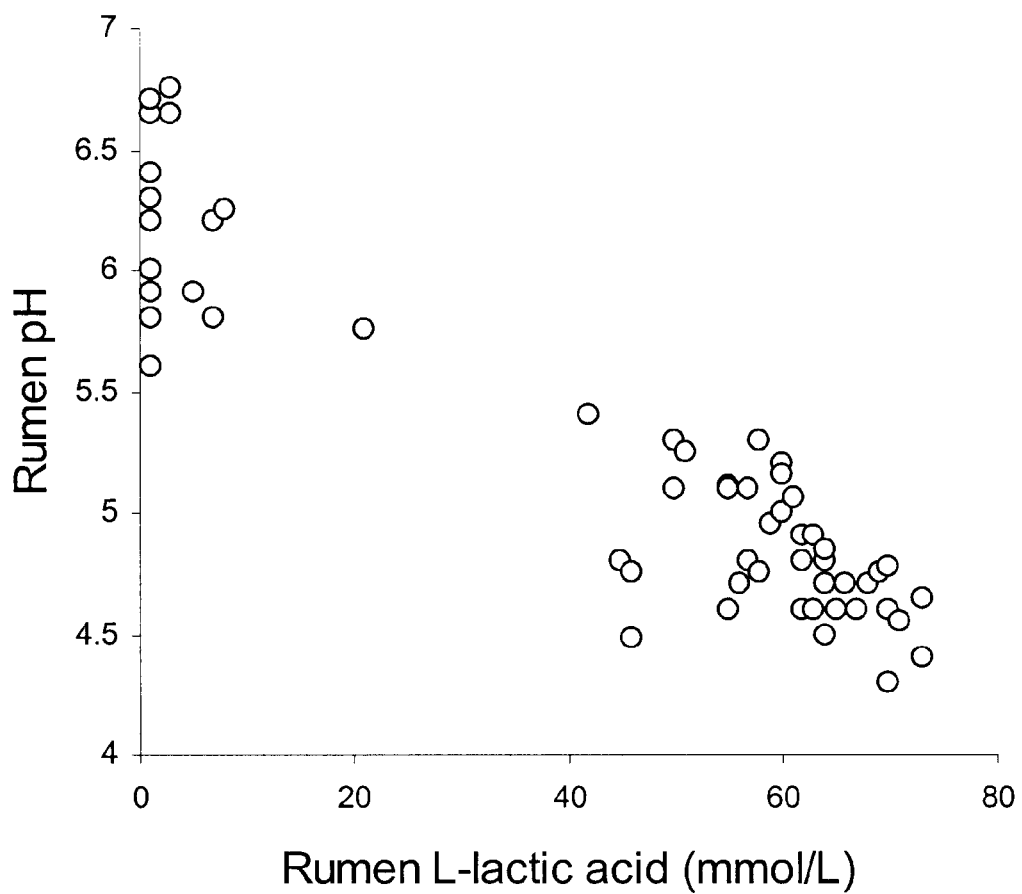
FIG. 1 illustrates the relationship between lactic acid concentration and rumen pH.
Figure 2:
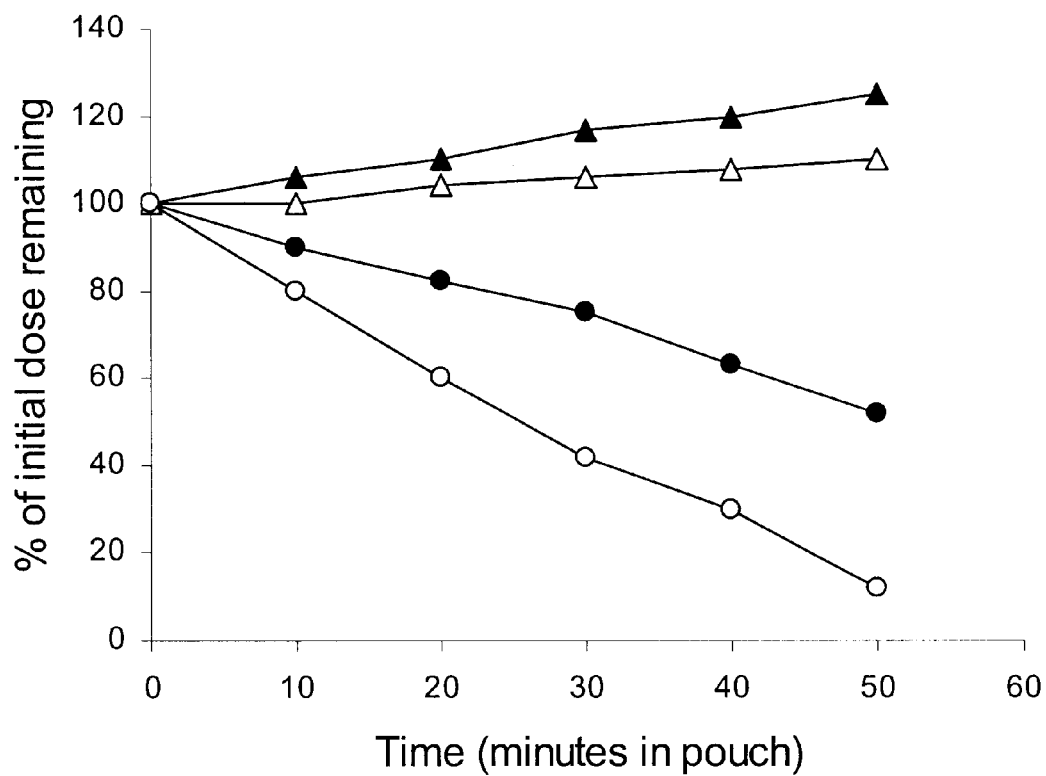

FIG. 2 refers to the absorption of lactic acid and volatile fatty acids (VFA) from the rumen and caecum. This shows a net gain in lactic acid over the same period when there is significant absorption of VFA. The significance of these data is that when lactic acid accumulates in the gut it is unlikely to be absorbed in the same way as the VFA, explaining why very low pH levels are common in the presence of lactic acid (see FIG. 1).

Figure 3:
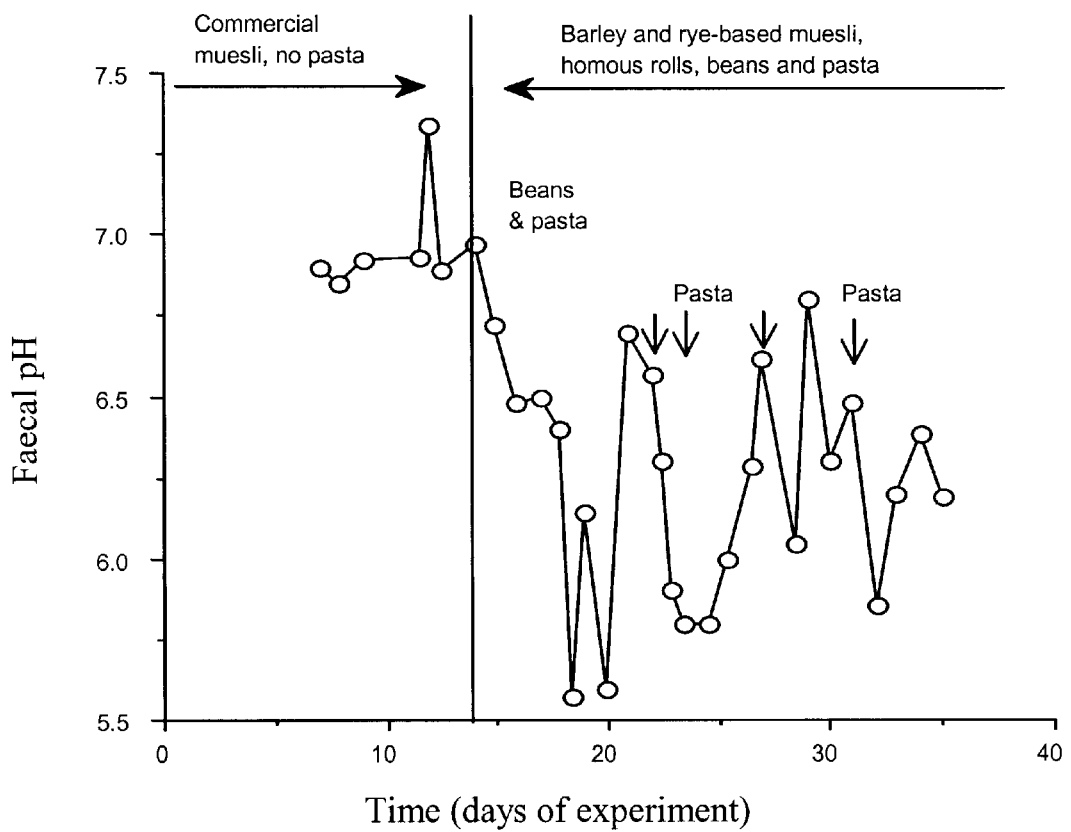

FIG. 3 refers to faecal pH measured over time in a mature male consuming a diet characterised by readily digestible carbohydrate low in resistant starch and non-starch polysaccharides for 2 weeks and then a diet considered to deliver higher levels of fermentable carbohydrate to the hind gut The main changes in the diet were in relation to the composition of the muesli (which was altered to contain higher levels of resistant starch and non-starch polysaccharides) eaten each morning, and the amount of pasta and beans. Arrows indicate the consumption of large pasta meals.

Figure 4:
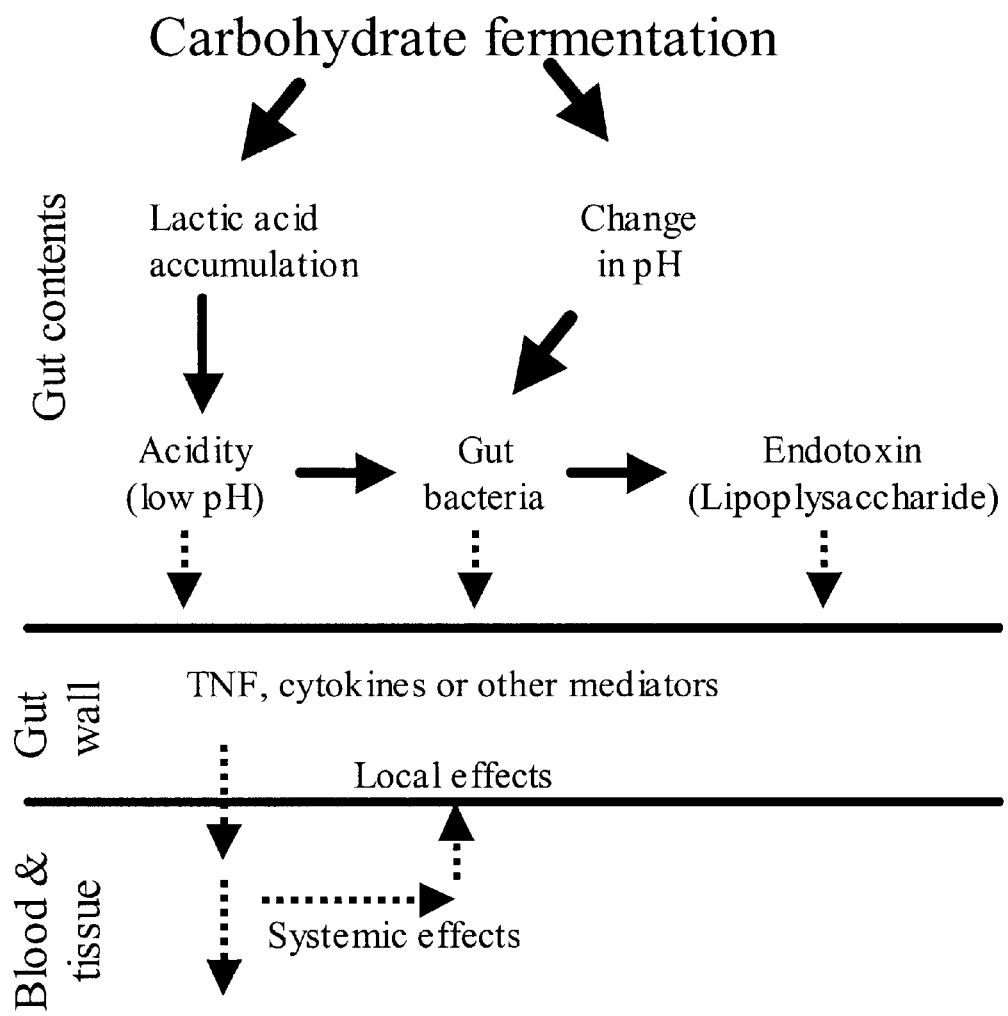

FIG. 4 shows that rapid carbohydrate fermentation and acidic conditions in the gut result in endotoxin (lipopolysaccharide) production. Acidic conditions and the presence of endotoxins within the gut challenge the host immune system via TNF, cytokine and/or other mediators to cause a range of local and system effects.

Figure 5:
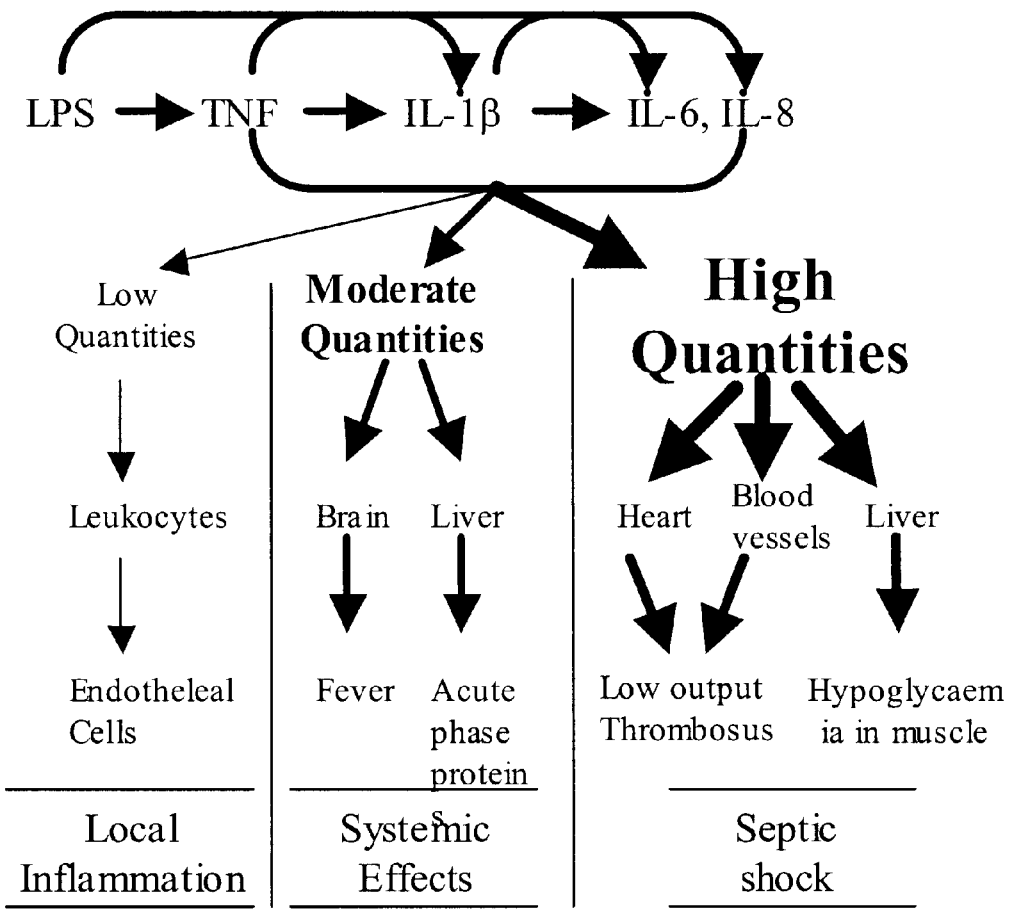

FIG. 5 shows some of the variable effects that can result from the primary stimulation of the immune system through bacterial lipopolysaccharides. It is important to note how the effect of LPS can be localised or can act systemically particularly so in the case of the gastrointestinal tract which is well provided with lymph nodes (GALT) able to amplify any immune stimuli from the gut. There is a far wider range of effects than summarised in this diagram and these include tissue remodelling (collagenase, diabetes mellitus and other proliferative and degenerative tissue conditions), coagulation system, kidney function, cachexia, appetite and others.

Figure 6:
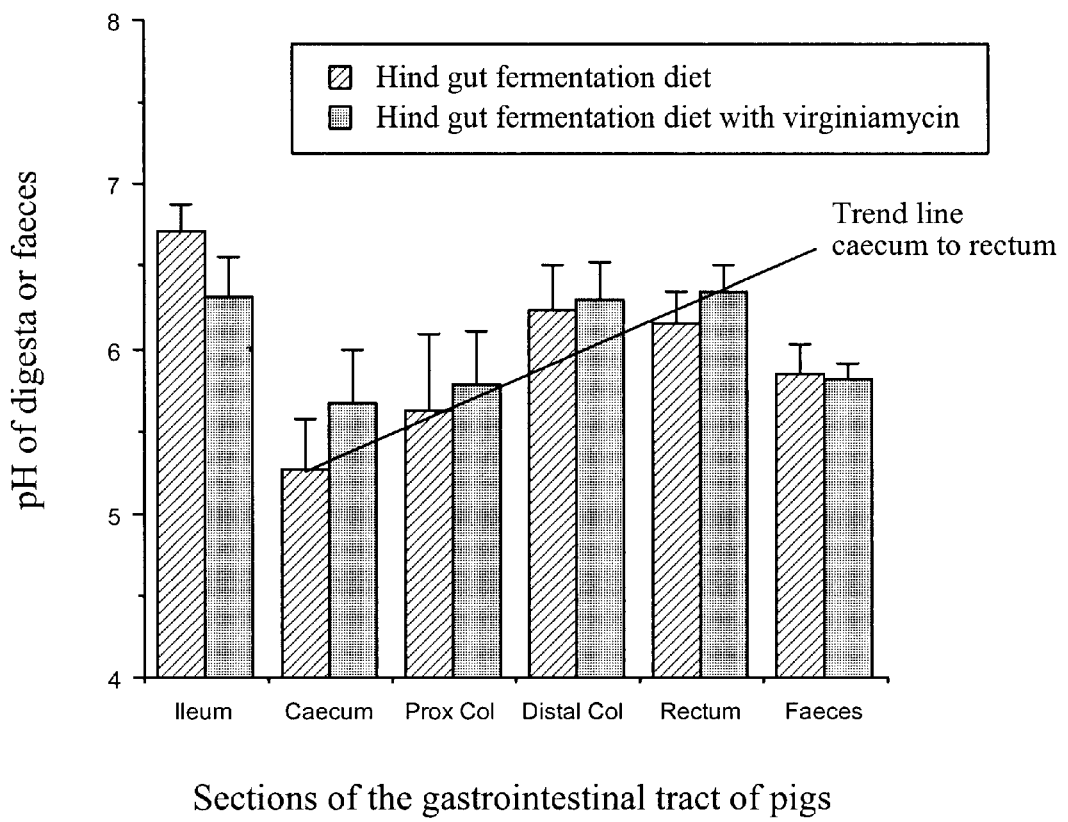
Figure 7:
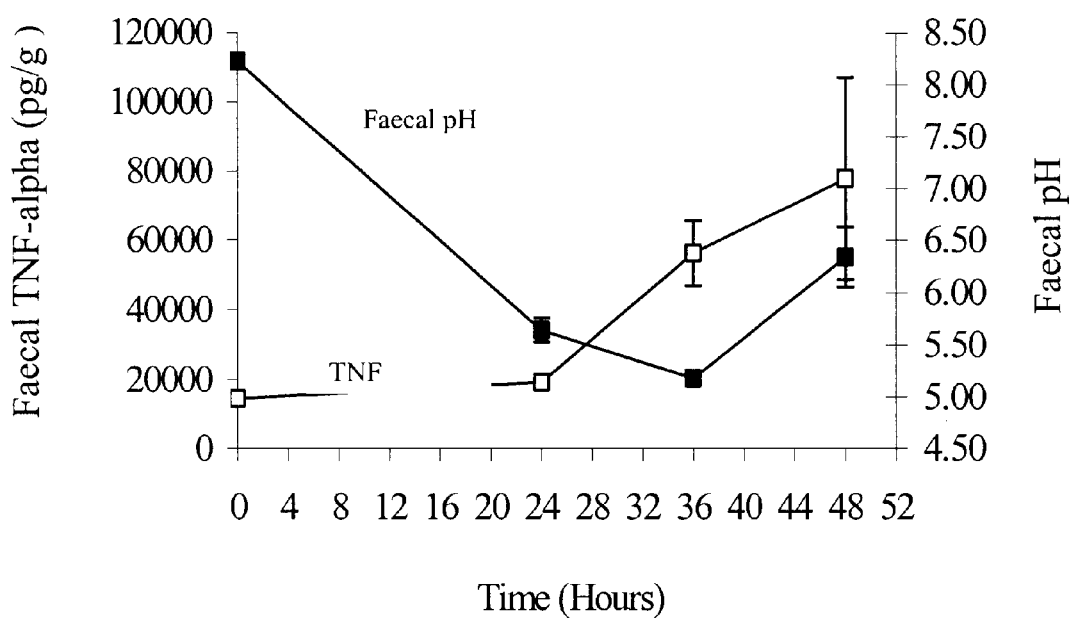

FIG. 6 shows pH measured in different parts of the digestive tract of pigs fed a diet promoting hind gut fermentation (HGF diet) with or without virginiamycin. Experimental details are described in Example 6. It is clear from FIG. 6 that virginiamycin has a consistent effect in reducing acid accumulation (increasing pH) in all parts of the digestive tract, and provides evidence for its use in the prevention and control of acidic gut syndrome in pigs FIG. 7 illustrates changes in faecal pH and TNF-α measured in sheep following ingestion of a pelleted diet containing a high concentration of barley with or without virginiamycin. Experimental details are described in Example 7

Figure 8:
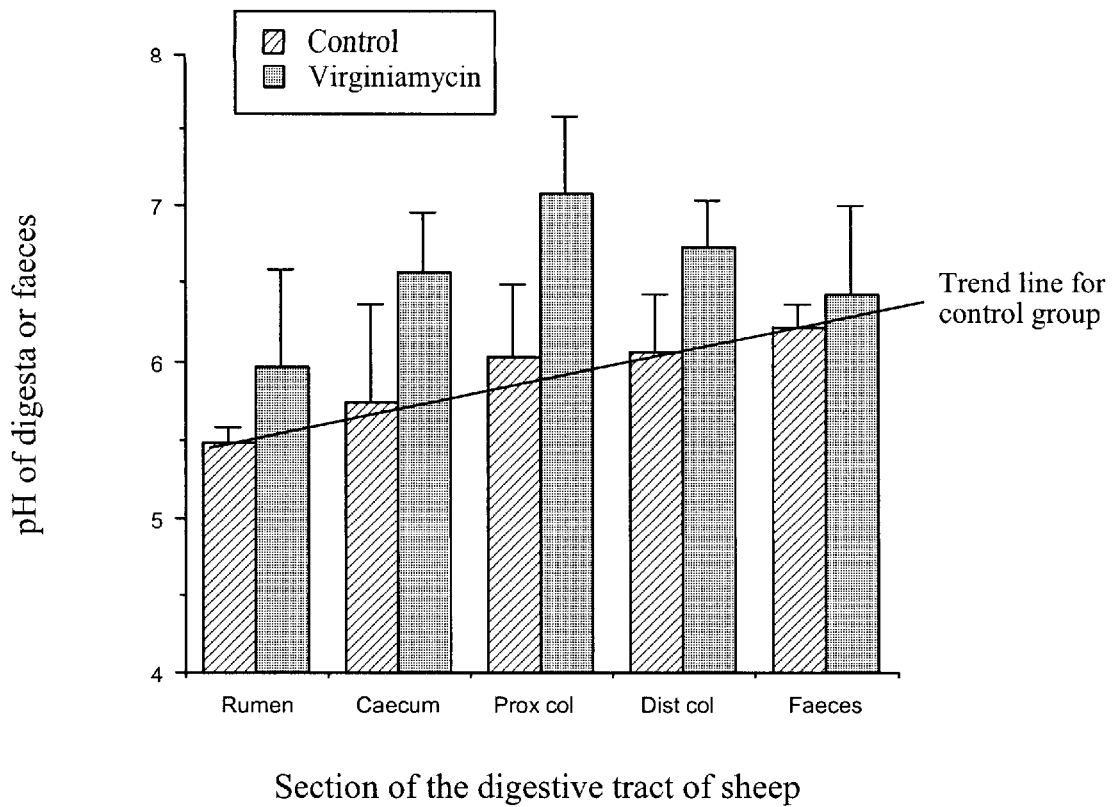

FIG. 8 indicates pH measured in different parts of the digestive tract of sheep following ingestion of a pelleted diet containing a high concentration of barley hind gut fermentation (HGF diet) with or without virginiamycin, wherein experimental details are described in Example 7. It is clear from FIG. 8 that virginiamycin has a consistent effect in reducing acid accumulation (increasing pH) in all parts of the digestive tract, and provides evidence for its use in the prevention and control of acidic gut syndrome in sheep.

Figure 9:
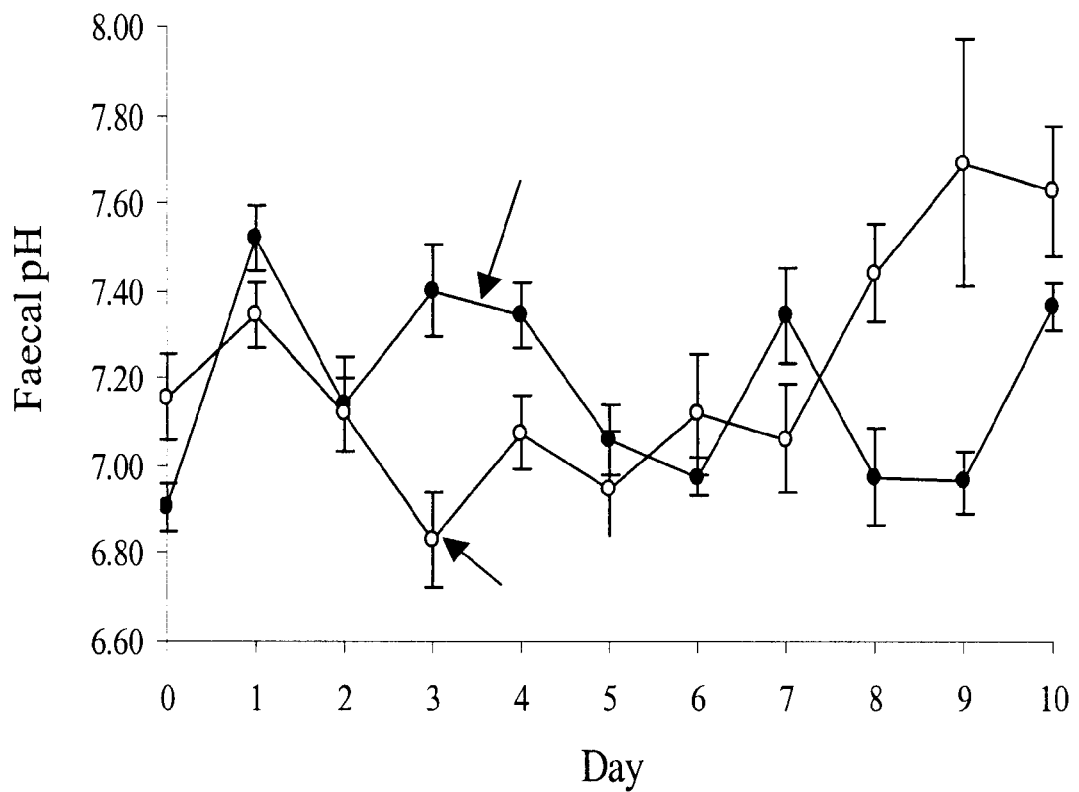
Figure 10:
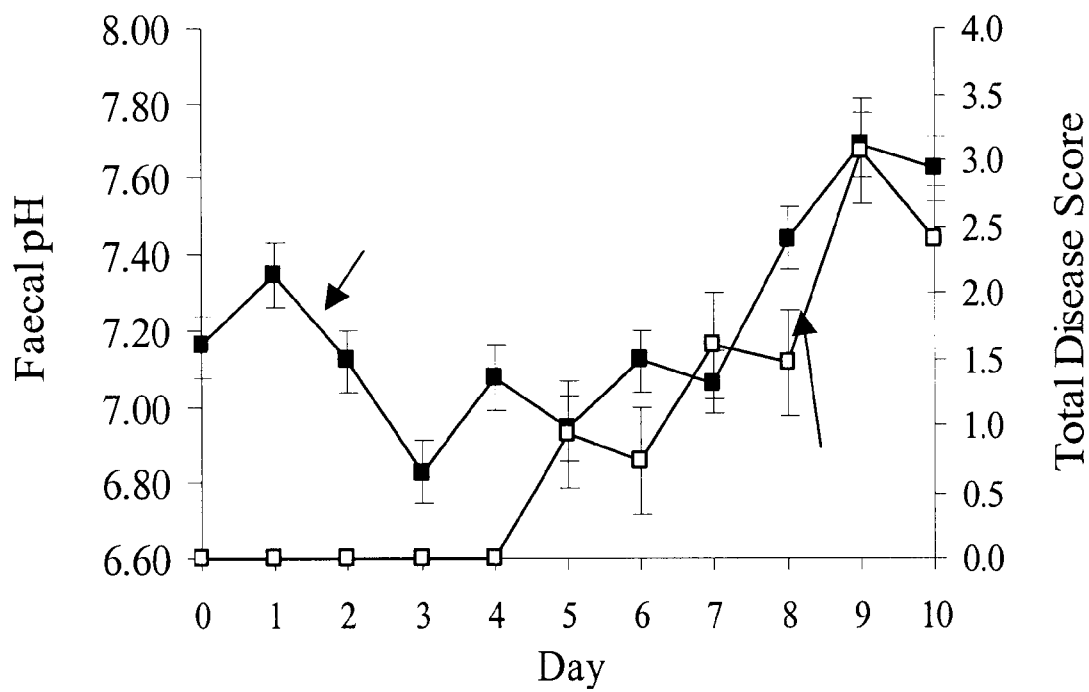

FIG. 9 describes faecal pH for mice given $H_2O$ without any additives (●) or given $H_2O$ containing 5% Dextran Sulphate in solution (○). Mice had free access to commercial mouse food at all times FIG. 10 illustrates faecal pH (■) and total disease score (□) for mice given $H_2O$ containing 5% Dextran Sulphate in solution. The disease score is based on assessment of diarrhoea, and the appearance of mucus and blood.

BEST MODE OR MODES OF PERFORMING THE INVENTION

Under certain dietary conditions, which until now have been considered normal, increased acid and endotoxins are produced by gut microbes which stimulate the immune-system in ways leading to local inflammation, systemic reactions related to immune diseases and perturbation of basement membranes in organs such as the respiratory system and the gastric stomach.

The current practices described above, do not recognise the risks associated with increased acid production and the effect that this is likely to have on the immune system of the host. Understanding the aetiology of the new condition, acidic gut syndrome, provides a foundation on which to develop a range of treatments based on methods to minimise gut acidity associated with fermentation and thereby reduce the adverse secondary consequences mediated via the immune system.

The present invention involves four stages or levels of new information which are often inter-connected and may be considered together.

Primary Effects Within the Gut

New experimental results show that lactic acid in the gut contents produce acidic conditions characterised by levels of pH below 5.5. As shown in FIG. 1, the pH of the rumen does not fall below 5.5 unless lactic acid is present. This pattern of fermentation within gastrointestinal systems applies in other parts of the gut and in other species. A reason for this is the fact that lactic acid is not absorbed from fermentation compartments in the digestive tract in the same way as other organic acids such as acetic, propionic and butyric (Ding et al., 1998; and see FIG. 2).

Levels of acidity characteristic of acidic gut syndrome can occur in the gut under relatively normal dietary conditions. shows changes in faecal pH over time in a healthy adult male, on a normal diet experiencing no discomfort and passing stools of normal consistency. These data show that the acidity of the hind gut in humans can reach levels which are almost certain to be associated with lactic acid and bacterial endotoxins. When dietary or digestive conditions result in rapid fermentation in the gut, both the absolute level of acidity (pH) changes but also the stability of pH. It should be emphasised that pH is a log scale and that a change from 6.8 to 5.8 represents a 10 fold increase in acid concentration. Short term changes in pH can lead to transitory increases endotoxins production within the gut and irregular changes in the level of challenge to the immune system.

Many dietary conditions considered healthy for humans, dogs and other species (high levels of fermentable fibre and inoculation with live lactic acid producing bacteria) result in the accumulation of lactic acid in several sections of the intestines (as shown diagrammatically in FIG. 4), wherein the low pH and bacterial endotoxins combine to stimulate the immune system of the host, and results in the disease conditions described above. It is important to emphasise that these interactions between endotoxins and low pH in the gut, to affect the gut wall can occur when normal diets are being used and when normal feeding regimes apply. Patterns of fermentation and levels of digesta pH previously thought to be normal and even desirable for the health and well being of the host are therefore predisposing factors in acidic gut syndrome in which the acidity and production of bacterial endotoxins and other potentially toxic substances have local and systemic effects via the gut.

Local and Systemic Effects

The effects of acidic gut syndrome are mediated primarily via TNF and related cytokine activity but may involve other aspects of the immune system and/or the endocrine system. An example of the effects of endotoxins (lipopolysaccharides) on TNF is summarised in FIG. 5. In small doses, cytokine activity causes local inflammation of the: gut, and with increasing doses of endotoxin, the cytokine produce numerous systemic effects which can influence almost all tissues, and forms the basis of many immune diseases the aetiology of which has not previously been known.

The tissues most affected by systemic cytokine activity are determined by genetic and functional factors and can also be affected by local tissue damage or physical sensitisation. Often cytokines affect more than one organ or tissue and it is common to find simultaneous problems for example in the lungs and skin (asthma and dermatitis) or skin and joint tissue (dermatitis and rheumatoid arthritis). Physical stress or irritation on joints or on other tissues can localise the action of the immune system and its agents. In this way injuries or other irritants can initiate reactions which are amplified by the underlying activities of the immune system including sub-acute inflammation. The origin of this elevated background immune system activity has not been previously understood and a number of disease conditions have had no known cause. The present invention therefore explains a wide range of immune diseases including chronic lung conditions, sensitisation to physical, chemical and biological irritants which cause allergic type reactions, certain forms of diabetes, problems with cartilage and connective tissue, effects on the pancreas, kidneys, thyroid and other organs of the endocrine system. It also covers immune conditions associated with localised inflammation of sections of the gut.

Endotoxins and the related TNF and cytokine responses can also stimulate glycolysis which, in turn, can lead to slightly elevated body temperature and systemic acidosis through the accumulation of L-lactic acid as a product of glucose utilisation by muscle and other tissues. This acidosis associated with TNF (Horohov et al, 1997) is not related to D-lactic acidosis which results from the absorption of lactic acid from the gut. This systemic acidosis can contribute to disruptions of normal mineral metabolism as the body needs to maintain anion/cation balances as well as constant blood pH. The elevated level of tissue metabolism associated with glycolysis can exacerbate problems of heat stress in hot and humid climatic conditions.

Since the cytokine activity also affects the brain, and via this route, the production of hormones such as prostaglandins (which are recognised in their stimulation of pyrogenic reactions) it is likely that the adverse effects of acidic gut syndrome extend to the impairment of the reproductive system and other functions which depend on hormonal control via the central nervous system. Impaired reproductive performance is an important problem in high producing dairy herds fed large quantities of grain to enhance milk production during early lactation (the time when the next mating is scheduled). It could also be a possible factor inhibiting pregnancy in certain women. This could be exacerbated by the stress and anxiety often associated with this situation, which would increase digesta flow rate and deliver high levels of fermentable carbohydrates to the hindgut, and increase the risk of acidic gut syndrome.

Mammary development and subsequent milk production in dairy cattle is reduced under dietary situations involving grain feeding. There is also a high incidence of mastitis and variable feed intake secondary problems of lameness and respiratory disease in herds fed high levels of grain. These conditions may be initiated and/or exacerbated by the acidic gut syndrome and alleviate d by its management and prevention.

The role of TNF-α in cachexia involves, in part, a reduction in feed intake and this response was also identified in Example 6 in pigs with acidic gut syndrome. A new method of treatment of cachexia, of previously unknown primary cause, can be now be treated by management and prevention of acidic gut syndrome. Loss in efficiency due to reduced feed intake in the production feeding of farm livestock is a serious problem which can be ameliorated by management and prevention of acidic gut syndrome.

Side Effects of Stress

In addition to the range of immune diseases described above there are further types of conditions covered in this invention which were previously thought to be associated with stress. One of the effects of psychological or physical stress is to increase the rate of digesta flow. More rapid digesta flow results in decreased residence time in the upper digestive tract and the passage of more undigested material passing to the lower tract. This increases the amount of fermentable substrate entering the hind gut and increases the risk of acidic gut syndrome described above. Although soft faeces and diarrhoea are well recognised as side effects of stress, the acidic nature of the faeces (and hind gut digesta) under these conditions have not been recognised as adverse and potentially dangerous factors which could lead to gut acidity and endotoxin production.

The effects of stress through acidic gut syndrome may have systemic effects on other parts of the digestive tract such as the gastric epithelium which can predispose the tissue to the development of gastric ulcers. This aspect of the invention is therefore based on the fact that the primary problem in the gut is caused by fermentation in the hind gut and not necessarily the over-producing of acid in the gastric stomach or the presence of *Helicobacter pylori*. The role of acid in the gastric stomach may act to exacerbate the primary effect of systemic effects of acidic gut syndrome.

In addition to gastric ulcers there are other adverse side effects of stress covered by this invention including predisposition to lung infections as a result of primary damage to the integrity of alveolar epithelium through cytokine and immune system changes initiated by acidity in the hind gut by systemic endotoxins of hind gut origin. Secondary effects also include hair and wool growth, hypertension and other factors which are mediated via the immune or endocrine system.

Furthermore, cold weather is also known to increase the rate of digesta flow. The increased risk of acidic gut syndrome is seen through increased incidence of arthritis and skin problems in winter.

The Effects of Acidity in the Mouth

Effects of lactic acid accumulation and microbial endotoxin production can occur in the most anterior portion of the gastrointestinal tract, that is, the mouth cavity itself. The teeth and gums can contain a rich microbial population able to produce significant amounts of lactic acid when sugars and starches are consumed. While it is widely recognised that lactic acid is produced around the teeth and gums leading to dental decay, it is not known that microbial endotoxins are produced at the same time. This effectively creates a form of acidic gut syndrome around the gums in which acidity and endotoxins may have similar local and systemic effects as have been described above.

The invention will now be described in greater detail by reference to specific Examples, which should not be construed as limiting on the scope thereof.

EXAMPLES

Examples 1 to 5

In general, one can refer to the accompanying FIGS. (1–5) for Examples 1 to 5 of the present invention.

FIG. 1 illustrates the relationship between lactic acid concentration and rumen pH. This shows that unless lactic acid is present the pH does not fall below 5.5.

FIG. 2 refers to the absorption of lactic acid and volatile fatty acids (VFA) from the rumen and caecum. This shows a net gain in lactic acid over the same period when there is significant absorption of VFA. The significance of these data is that when lactic acid accumulates in the gut it is unlikely to be absorbed in the same way as the VFA, explaining why very low pH levels are achieved in the presence of lactic acid (see FIG. 1).

FIG. 3 refers to faecal pH measured over time in a mature male consuming a diet characterised by readily digestible carbohydrate low in resistant starch and non-starch polysaccharides for 2 weeks and then a diet considered to deliver higher levels of fermentable carbohydrate to the hind gut. The main changes in the diet were in relation to the composition of the muesli eaten each morning and the amount of pasta and beans. Arrows indicate the consumption of large pasta meals.

FIG. 4 shows that rapid carbohydrate fermentation and acidic conditions in the gut result in endotoxin (lipopolysaccharide) production. Acidic conditions and the presence of endotoxins within the gut challenge the host immune system via TNF, cytokine and/or other mediators to cause a range of local and system effects.

FIG. 5 shows some of the variable effects that can result from the primary stimulation of the immune system through bacterial LPS. It is important to note how the effect of LPS can be localised or can act systemically. There is a far wider range of effects than summarised in this diagram and these include tissue remodelling (collagenase, diabetes mellitus and other proliferative and degenerative tissue conditions), coagulation system, kidney function, cachexia, appetite and others.

Example 6

Acidic Gut Syndrome in Pigs

Aim:

An experiment was conducted to investigate acidic gut syndrome in the pig and the side effects mediated via the immune system. The build-up of acid in hind gut digesta of pigs has been reported in relation to perceived benefits of increased caecal and colonic fermentation of starch high in amylose and of low intestinal digestibility (Brown & McNaught, 1997). However, no previous study suggests that accumulation of acid in the hind gut of pigs during fermentation of dietary carbohydrate may, in fact be harmful. The aim of the present study was to investigate whether acid accumulation in the hind gut is a primary factor leading to a wide range of adverse effects on the health and welfare of the pig.

Hypothesis:

This experiment was based on the hypothesis that rapid fermentation of carbohydrate in the hind gut can lead to accumulation of acid and low pH which, in turn, stimulates gut cytokine activity leading to local and systemic stimulation of the immune system with adverse effects on all systems of the body sensitive to immune system activity. It is possible that the stimulation of cytokine activity by low pH in the hind gut can occur directly through increased concentrations of acid, and/or indirectly through increased endotoxin concentrations, and it is possible that both low pH and endotoxins act additively or synergistically.

Explanation of Experimental Model:

It is often assumed that the digestive enzymes of the stomach and small intestine are able to breakdown all dietary starches and sugars to glucose and that the absorptive capacity of the small intestines is sufficient to ensure that no glucose passes to the caecum and colon. These assumptions are not always correct and there is practically always some carbohydrate which passes undigested to the hind gut, where it is fermented and produces organic acids. The objective for the control (basal) diet was to minimise the amount of undigested starch passing to the hind gut. For this reason boiled rice was selected, which is one of the most digestible sources of starch to use as the main source of carbohydrate for the control diets. Rice contains practically no non-starch polysaccharides and, if properly cooked, is almost completely digested before reaching the hind gut. In this way, hind gut fermentation of dietary starch in the control group of pigs was minimised, and thereby minimizing acid accumulation, maintaining high pH, and minimising the risk of acidic gut syndrome.

Oligosaccharides consist of relatively short chains (3 to 10) of simple sugars in configurations not normally subject to enzymatic breakdown in the stomach and small intestine and they pass intact into the caecum and colon where, because of their solubility, they are rapidly fermented. Raftilose is a fructo-oligosaccharide extracted from beet root and was selected for inclusion in those diets designed to produce rapid hind gut fermentation and an elevated risk of acidic gut syndrome. A combination of rice and raftilose gives a semi-purified diet with the potential to vary the extent of carbohydrate digestion between the small intestine and caecum/colon. A second source of indigestible carbohydrate was provided by high-amylose maize. Elevated levels of amylose in maize starch makes it less digestible in the small intestine than normal maize starch but provides carbohydrate which is rapidly fermented in the hind gut. High-amylose maize was included together with raftilose to increase the amount of fermentable carbohydrate entering the caecum and colon.

Studies of rapid carbohydrate fermentation and acid build up in the hind gut of sheep and horses have shown that the concentration of volatile fatty acids (VFA) starts to increase and pH starts to drop before there is a proliferation of gram positive bacteria (particularly *Streptococcus bovis* and Lactobacilli) capable of producing lactic-acid. Lactic acid is a stronger acid than the VFA and is not absorbed from the caecum as quickly as VFA, and this combination of factors leads to low pH which is the first step in development of acidic gut syndrome. Virginiamycin was included in the diet of one of the two dietary treatments containing raftilose and high-maize starch to investigate its effectiveness in controlling lactic acid accumulation and hind gut pH as a potential method for preventing or controlling acidic gut syndrome.

Experimental design and treatments

There were three dietary treatments:

| 1 | Control | Boiled rice, with protein and mineral supplement to provide a well balanced diet for young weaner pigs. |
|---|---|---|
| 2 | Hind gut fermentable (HGF) | Boiled rice, high-amylose maize and raftilose as the sources of carbohydrate and a protein and mineral supplement to provide a well balanced diet for young weaner pigs. |
| 3 | HGF diet with virginiamycin | This dietary treatment was identical to the HGF diet described above except that Eskalin Premix (Pfizer, Australia) was added to the diet to provide 25 mg virginiamycin/kg dietary dry matter (DM). |

Study Animals and Management of Pigs

Breed and No.: 18 Large White/Landrace/Duroc/Hampshire cross

Sex and age: mixed sex weaners (4 weeks) taken from two litters

Pigs were weaned at 4 weeks of age and housed individually in pens with concrete floors with weld mesh dividing walls in temperature controlled facilities. The pens were cleaned twice per day and drinking water was provided by an automatic watering system. All animals were handled daily to acclimatise them to experimental procedures associated with sampling.

Experimental Diets and Feeding

Piglets were fed ad libitum on the basal diet for two weeks until commencement of dietary treatments. The diets were formulated to ensure balanced provisions of nutrients for growth and contained 67.5% carbohydrate (rice, cornflour and raftilose) and 32.5% protein mix. The protein mix contained 55% meat meal, 32% fishmeal, 6% casein and 6% vitamins, oil and synthetic amino acids. The proportion of total carbohydrates contributed by rice, corn flour and raftilose on each day of the study is shown in Table 1 together with the total amount offered per pig.

TABLE 1

Amount of feed offered each day during the experimental period and the percentage of total carbohydrate contributed by rice, corn flour and raftilose on each day.

| | Feed offered | Percentage of each carbohydrate in HGF diet (% of DM) | | |
|---|---|---|---|---|
| | (g DM/pig) | Rice | Corn flour | Raftilose |
| Day 0 | 301 | 33 | 45 | 22 |
| Day 1 | 301 | 33 | 45 | 22 |
| Day 2 | 327 | 27 | 37 | 36 |
| Day 3 | 384 | 32 | 0 | 68 |
| Day 4 | 439 | 36 | 0 | 64 |
| Day 5 | 521 | 34 | 0 | 66 |
| Day 6 | 521 | 34 | 0 | 66 |
| Day 7 | 522 | 27 | 0 | 73 |
| Day 8 | 583 | 22 | 0 | 78 |

Measurements

1. Daily collection of faeces from the pens of each pig to assess faecal consistency and for measurement of pH. Faecal consistency was assessed on a scale 1 to 5 with 1 being liquid diarrhoea and 5 being dry, separate, well formed faeces.
2. Collections of blood from the jugular vein (10 mL) were made on the mornings of days 1, 2, 6 and 8 of the study period for measurement of IL-1, white blood cell counts and differentiation, and acute phase protein.
3. Body weights were measured 2 days before the start of feeding experimental diets, on day 3 and day 7.
4. The body temperature of each animal was measured on days 0, 2, 5 and 7.
5. The amount of feed not consumed was measured each afternoon and intake calculated as a % of amount offered.
6. Animals were observed daily for any signs of abnormal behaviour or ill-health.
7. On day 7, half of the pigs in each treatment group were euthanased with pentobarbitone. Post mortem measurements were made of size of the digestive tract, the pH of digesta in different part of the tract and the digestive tract and other organs were examined for any sign of abnormal tissue appearance. On day 8 the remaining pigs were euthanased and the same post mortem measurements made on these animals.

8 Samples of digesta were stored for subsequent analysis of VFA and lactic acid concentration.

TABLE 2

Summary of results defining the build up of acid within the gut and the consequent changes in the immune system and the consequent effects on performance and health of the animals

|  | Control | Hind gut fermentation diet (HGF) | HGF with virginiamycin | Prob. Value |
|---|---|---|---|---|
| Acid accumulation |  |  |  |  |
| Caecal pH | 6.4$^a$ | 5.3$^b$ | 5.7$^{ab}$ | 0.03 |
| Rectal pH | 6.8$^a$ | 6.1$^b$ | 6.3$^b$ | 0.01 |
| Faecal pH (day 2) | 6.9$^a$ | 6.1$^b$ | 6.3$^b$ | 0.03 |
| Faecal pH (day 5) | 6.5$^a$ | 5.9$^b$ | 6.0$^b$ | 0.05 |
| Average faecal pH | 6.7$^a$ | 5.9$^b$ | 6.0$^b$ | 0.001 |
| Faecal consistency (av d1–5) | 4.65$^a$ | 2.89$^b$ | 3.53$^c$ | 0.001 |
| Bacterial changes |  |  |  |  |
| Caecal Lactobacilli | $1.3 \times 10^9$ | $6.5 \times 10^9$ | $1.4 \times 10^{10}$ |  |
| Caecal Strep. Bovis | $5.0 \times 10^7$ | $4.1 \times 10^9$ | $3.2 \times 10^9$ |  |
| No acid effect before hind gut |  |  |  |  |
| Ileal pH | 6.7 | 6.7 | 6.3 | ns |
| Stomach pH (days 8/9) | 4.0 | 3.9 | 3.6 | ns |
| Changes in immune system |  |  |  |  |
| Neutrophils (N) | 6.3 | 9.6 | 6.2 | 0.11 |
| Lymphocytes (L) | 14.0 | 11.0 | 11.0 | 0.06 |
| N:L ratio | 0.47$^a$ | 0.95$^b$ | 0.57$^a$ | 0.02 |
| Acute phase protein CD3 | 7.5 | 5.8 | 5.9 | 0.11 |
| IL-1 (day 5) | 1.8 | 2.4 | 2.0 | ns |
| IL-1 (av. days 1, 2, 5 & 8) | 2.0 | 2.2 | 1.6 | ns |
| Physiological and production effects of acidic gut syndrome |  |  |  |  |
| Intake (% offered) (day 4) | 88$^a$ | 59$^b$ | 81$^{ab}$ | 0.04 |
| Av intake (days 1 to 8) | 92$^a$ | 78$^b$ | 83$^{ab}$ | 0.07 |
| Weight change (days 3 to 7) | 1.18 | 0.73 | 1.13 | 0.02 |
| Weight of washed gut (g) |  |  |  |  |
| Stomach | 135 | 110 | 115 | 0.09 |
| Caecum | 24.7$^a$ | 39.1$^b$ | 31.4$^a$ | 0.002 |
| Rectum | 25.6 | 40.9 | 35.1 | 0.06 |

The main findings of the study are described below with reference to the data described in Table 2.

Validity of the Carbohydrate Model used to Study Acidic Gut Syndrome.

In pigs fed the HGF diet there were clear indications of acid accumulation in the hind gut as shown by lower pH in the faeces, rectal and caecal digesta, indicating accumulation of acid as a result of raftilose and corn flour inclusion in the diet. The lower faecal pH was closely related to increases in the populations of gram positive acid producing bacteria and the incidence of diarrhoea (lower faecal consistency scores). The fact that there were no differences due to diet in the pH of stomach or ileal digesta is of major significance. Lack of difference in these parameters shows that there was no accumulation of acid (no differential effects due to fermentation of carbohydrate) prior to fermentation of raftilose and/or starch in the caecum and colon. The effects of the different sources of carbohydrate can therefore be attributed to the different rate and extent of bind gut fermentation on the HGF diet leading to an accumulation of acid and a drop in pH.

As seen in Table 1, there was an increase in the proportion of raftilose in the carbohydrate fraction of the HGF diet between the beginning and the end of the study. This decision to increase the amount of raftilose in the diet was based on the fact that on day 1 of the study there was a high incidence of diarrhoea in pigs on the HGF diet, whereas on day 2, faecal consistency and pH appeared normal. In order to maintain rapid fermentation and low pH in the hind gut the concentration of raftilose was increased. This pattern of diarrhoea followed by relatively normal faeces was repeated on days 3 and 4 and for this reason the proportion of raftilose was again increased. No adverse effects, other than diarrhoea and low faecal pH, were observed in the pigs fed raftilose, and the nutritional model therefore appears to be well suited to the study of acidic gut syndrome, where the signs of hind gut acid accumulation (mainly diarrhoea) are often taken as 'normal' minor problems for which there is no cure.

Validity of the Model using Virginiamycin to Reduce Acid Build Up.

Virginiamycin was effective in reducing the extent of acid accumulation in the hind gut and in faeces (see FIG. 6). The results in relation to faecal consistency show how the virginiamycin significantly improved faecal consistency. The fact that the amount of acid in the faeces and hind gut digesta, and faecal consistency of the pigs were consistently between the results for pigs on the rice-based diet and those on the HGF, diet without virginiamycin, shows a clear beneficial effect of virginiamycin in reducing the accumulation of acid, and establishes a method for overcoming problems in relation to acidic gut syndrome at its source. In the present study the effect of virginiamycin in reducing acid accumulation on the HGF diet adds to the experimental design since there are clearly three levels of acidic gut syndrome produced by the treatments of: rice only, HGF with virginiamycin and HGF on its own. The fact that virginiamycin acts to reduce lactic acid production, and thereby acid accumulation, allows regression analysis of acid levels against other changes in the gut physiology without complication from the effects of other dietary factors. On the basis that there were two levels of lactic acid and two levels of pH and acidic gut syndrome on exactly the same diet, allows interpretation of the results on the basis of acid build up alone without complications associated with the possible side effects of proteins and the potential allergic reactions which have been attributed to gluten and other proteins considered to have harmful effects.

Immune System Responses

There were significant changes in the immune system in response to acid build up in the hind gut. The most notable change in the immune system was the twofold increase in the neutrophil to lymphocyte ratio in pigs on the HGF diet. This was a result of increased neutrophil numbers and a decrease in lymphocytes. There were increases in the levels of IL-1 in pigs fed the HGF diet. The changes in neutrophil levels were apparent from day 1 of the study and indicate an early effect of acidic gut syndrome on the immune system as a mechanism for effecting systemic changes. Many changes in the immune system are transitory and it is possible to miss peaks of cytokine and white blood cells in response to non-continuous stimuli. A significant change in any aspect of the immune system is therefore an important indication of the biological pathway by which hind gut acid build up can affect the systemic system.

Post Mortem Findings

Two of the pigs fed on the HGF diet had clear lesions in the lungs. While this was not statistically significant it does suggest a link with HGF diets. Further, there were two clear diet related changes noted on post mortem. These were the size and appearance of the caecum in pigs fed the HGF diet and the incidence of parakeratosis in the oesophageal zone in the stomachs of the same animals. These changes are considered to be most significant. The changes in the caeca (increased washed weight, wrinkling upon cooling and occasional signs of inflammation and haemorrhaging) could be explained by the increased acidity and fermentative activity within the organ. The very high incidence of parakeratosis in pigs fed the HGF diet is significant because it is the first stage in development of gastric ulcers (Kavanagh, 1994), and occurred in the absence of any changes in the pH of the stomach related to pH or dietary carbohydrate. It therefore appears that the diet-related damage to the oesophageal region of the stomach was caused by the primary effect of the HGF diet through rapid fermentation and a build up of acid in the hind gut The tissue changes in the caecum in response to increased fermentation and consequent acidic conditions, in addition to signs of frank inflammation in some animals, suggests the hind gut as the tissue responsible for stimulating the immune response. The rich supply of lymph nodes in the gastrointestinal mesentery provides the mechanism to multiply the hind gut immune response to make it systemically significant. Changes to membranes and epithelial surfaces are well established as consequences of acid build up in the gut of ruminants and horses. The rumen epithelium becomes detached during severe fermentative acidosis in sheep and cattle, and in horses the hoof becomes detached from the pedal bone during development of laminitis following fermentative acidosis in the hind gut. The discovery in this study that hind gut acid accumulation can cause parakeratosis in the stomach (the first stage towards ulceration) provides strong evidence that acid accumulation in the gut can bring about significant changes in membrane/epithelial structures; and that these changes can occur in other parts of the body distant to the site of acid accumulation.

Stomach ulcers were traditionally considered to be caused solely by elevated concentrations of acid in the stomach, and more recently *Helicobacter pylori* was identified as having an important role in the development and maintenance of stomach ulcers. The results of the study reported here indicates an important role of the immune system in changing the characteristics of the gut wall which creates suitable conditions for establishment of *Helicobacter pylori* and development of ulcers. This finding of the role of the immune system as a primary factor in the development of ulcers links three known predisposing factors for the formation of ulcers.

1. Stress is well known as a predisposing factor in ulcer formation and it is also known to increase the ratio of neutrophils to lymphocytes (Puppe et al., 1997). It is likely that these and other immune system factors act to bring about the first changes in the gut wall which predispose it to the development of ulcers.
2. Certain diets are known to cause ulcers in pigs. These diets are characterised by having high concentrations of finely ground cereal grain and are pelleted (Kavanagh, 1994). These features are likely to deliver substrate for extensive hind gut fermentation and acid accumulation is likely to stimulate immune system as described above.
3. The use of antibiotics is often associated with development of stomach ulcers. While antibiotics themselves are unlikely to cause ulcers they are always used when there is an infection which can be of sufficient severity to cause systemic changes in cytokines and other aspects of the immune system. These infections are likely to have the same systemic effects on the stomach as seen to arise from acidic conditions in the hind gut with both primary effects (gut acid and infection) stimulating cytokines. A survey of pigs at slaughter showed increased levels of neutrophils and reduced lymphocytes in animals with inflammatory conditions such as pleuritis or pneumonia (Odink et al., 1990). These changes in the immune system were similar to those observed in the current study in response to acid accumulation in the hind gut.

FIG. 6 illustrates the change in pH of digesta through the gastrointestinal tract to the faeces. It is clear from FIG. 6 that virginiamycin has a consistent effect in reducing acid accumulation (increasing pH) in all parts of the digestive tract, and provides evidence for its use in the prevention and control of acidic gut syndrome in pigs and sheep.

FIG. 6 also shows that changes in faecal pH are likely to give a very conservative estimate of the severity of acidic gut syndrome. The pH in the caecum and proximal colon is very much lower than in the rectum or faeces. The difference between the faecal/rectal pH and the caecal/proximal colon is nearly one pH unit (10 fold increase). Therefore, what might appear as a relatively minor drop in faecal pH from 7.0 to 6.5 is likely to represent a drop in caecal pH from around 6.8 down to 5.5.

Feed Intake and Liveweight Change

There were clear links between the HGF diet, consequent build up of acid, the incidence of diarrhoea and feed intake and liveweight gain. The more severe the acidity and diarrhoea the greater the decrease in feed intake. There were no signs that the palatability of the HGF diet was affected by incorporation of raftilose. The higher intake by pigs treated with virginiamycin (less acid accumulation and less severe diarrhoea), further indicates that factors other than palatability reduced feed intake. While the biological pathway linking hind gut acid accumulation and reduced intake is not clear it is possible that changes in the immune system, and particularly IL-1 could be responsible. This discovery of reduced feed intake in response to acid build up within the hind gut offer a new explanation for low, and variable, feed intake and low efficiency in the production feeding of farm livestock.

Behavioural Changes

There were two cases of tail biting during the study and the pigs involved were all in the treatment groups fed the HGF diet. The biting occurred through the wire mesh dividing the pens. Increases in the neutrophil:lymphocyte have been found in association with increased agonistic behaviour in pigs and again suggest involvement of the immune system.

Conclusions

The study provides clear evidence that acid accumulation in the hind gut, caused by rapid fermentation of undigested dietary carbohydrate, can stimulate the immune system in similar ways as observed during inflammatory infections and stress. The only overt signs of acidic conditions in the hind gut were diarrhoea and intermittent diarrhoea is not considered as an animal health problem. The links identified in this study between hind gut acidity, the immune system, parakeratosis (the first stage of ulcer formation) and physical and physiological changes in the hind gut form the basis of acidic gut syndrome.

Based on these results, there is strong evidence to suggest that acidic gut syndrome is associated numerous other secondary changes developing from this condition, such as:

Arthritis and joint conditions where the immune system is implicated;

Susceptibility of the gut to parasitic infections through changes in the epithelium disrupting its integrity and facilitating establishment of bacteria, fungi and helminths in the gut wall;

Lung infections. Pneumonia is well established as a concurrent disease with gastric ulcers in pigs (Kavanagh, 1994) and acid gut syndrome could be a predisposing condition for both disease conditions;

Bleeding in the lungs following strenuous exercise results from damage to the alveolar tissue which could be potentiated by changes to the immune system caused by acidic gut syndrome;

Asthma and skin conditions associated with changes in the immune system could be caused or exacerbated by acidic gut syndrome;

Auto-immune conditions could also initiated or exacerbated by acidic gut syndrome;

Any conditions related to inflammation of the gut such as appendicitis, Crohn's disease, inflammatory bowel disease, colitis and chronic diarrhoea. Direct effects of acidity and endotoxins on the gut wall may lead to these inflammatory conditions. It is also possible that indirect effects may predispose development of appendicitis and other inflammatory conditions in the same way as parakeratosis (stomach ulcers) were observed to develop in the current study; and Reduced feed intake in response to acid accumulation in the gut, shown in this study, could have serious implications for production feeding systems and prevention of acidic gut syndrome is likely to produce significant improvements in productivity.

Example 7

Acidic gut syndrome: evidence of an inflammatory response releasing the cytokine TNF-α

Background and Hypothesis

It is known that endotoxins are present in the rumen of ruminant animals (Dougherty et al., 1975) and in the hind gut of horses. Experiments in which endotoxins have been administered to the gut have not produced any adverse effects on animal health and it has been concluded that they do not cross the gut wall. For this reason the consequences of fermentative acidosis in the gut have been explained in terms of the absorption of acids and systemic acidosis (Dunlop, 1972; Blood et al., 1983, Nocek, 1997).

Hypothesis and Implications

The hypothesis on which the current study was based is that the accumulation of acid and low pH can combine with bacteria and endotoxins in the gut to produce an inflammatory response which transforms the gut and its contents to a status equivalent to septicaemia in which intact bacteria or their toxins gain access to the host's tissues and the systemic circulation. TNF-α is known to play a pivotal role in initiating systemic toxaemic reactions during endotoxaemic sepsis, but its role in mediating effects of acid accumulation in the hind gut has not previously been identified. If TNF-α is produced in response to fermentative acid accumulation in the gut, then there is a clear case for implicating acidic gut syndrome as a contributor to the many consequences of systemic cytokine activity known to be associated with elevated levels of TNF-α.

TNF-α

Tumour Necrosis Factor (TNF) is a 17kD polypeptide, which is a member of the cytokine family. TNF is also known as cachectin, and referred most commonly to by its circulatory form, TNF-α. TNF-α receptors can be found in almost all cells in the body (Beutler et al., 1985). In small amounts, TNF-α causes tissue remodelling and local inflammation (Tracey et al., 1989). If large amounts are present it can be released into the blood and act as an endocrine hormone (Abbas et al., 1996), leading to cachexia (wasting), tissue injury and irreversible shock and death (Tracey et al., 1989) (Tracey and Cerami, 1993). TNF-α is also known to be found in very high levels in patients with inflammatory Bowel Disease (IBD), especially Crohn's disease (Murch et al., 1991; van Deventer, 1997) and is suspected to mediate many of the effects of IBD including cachexia.

When TNF-α is released in large amounts and it acts in the blood, significant levels are also released back into the lumen of the gut. Recently, TNF-α has been reported in the faeces of children with IBD as a marker of intestinal inflammation and disease severity (Braegger et al., 1992); (Nicholls et al., 1993) indicating that mucosally produced TNF-α is also released into the gut. (Braegger et al., 1992) report that children can normally have between 15 and 100 pg TNF-α/g faeces. In children with active Crohn's disease, TNF-α can be as high as 10,000 pg/g faeces. In this study, faecal TNF-α was measured in animals fed grain to determine if a build up of acid in the gut produced TNF-α in a similar way as occurs in colitis and sepsis.

Experimental Design And Feeding Regime

Animals Housing and Feeding

Six full mouth cannulated cross-bred sheep, weighing approximately 45 kg were used in the trial. These sheep were housed in individual pens on a wood grating floor in an enclosed animal house. All sheep were fed once per day, and water was available at all times ad libitum. All sheep were fed a basal diet consisting of oaten chaff plus 1% urea and 1% mineral pre-mix (Pfizer Animal Health Pty. Ltd.). At time 0 in the experiment, all sheep were fed a pellet containing high levels of barley with or without virginiamycin (VM). The sheep were autopsied 48 hours after grain feeding.

Dietary Treatments

All sheep were offered 1000 g of a pellet containing 76% barley, 17% lucerne, 3.5% cottonseed meal, 1% urea and 1.5% limestone at the start of the experiment. The sheep were then offered another 1000 g of the pellet 12 hours later. All sheep consumed all of the pelleted feed offered. Half of the sheep received the pellets with no dietary additives, and the other half received the pellets with virginiamycin (VM) added at 30 mg/kg. Eskalin (Pfizer Animal Health Pty. Ltd., 20 g virginiamycin/kg) was included at 1.5 g/kg pellets to provide 30 mg VM/kg in the mixed diet. The animals were monitored closely after receiving grain and autopsied 48 hours after initial grain feeding.

Samples and Collections

All sheep were fitted with faecal collection bags, which consisted of a PVC ring attached to the posterior of the sheep to which a plastic bag was attached in order to collect total faecal output. Rumen fluid was taken via the rumen fistula. Rumen and faecal samples were taken at 4 hourly intervals for the first 12 hours after grain feeding. Samples were then taken at 24, 36 and 48 hours after initial feeding.

Sample Analysis

Rumen Fluid

Rumen fluid pH was analysed immediately using a portable pH meter ('Piccolo 2' ATC pH meter by Hanna Instruments). A sample was also added to a 20 mL McCartney bottle containing approximately 7 μL of concentrated $H_2SO_4$, and frozen for later analysis of lactic and volatile fatty acids.

Faeces

A representative 20 g sample of faeces was taken into a small vial, an equal volume of water added and mixed well. The faecal pH was then measured immediately on this sample as for rumen fluid. A further sample was placed in a sterile container and an equal weight of deionised water added to it. This was mixed well using a sterile spatula, and then centrifuged at 15000 rpm for 20 mins. The supernatant was then transferred using a sterile pipette to 3 individual microfuge tubes and frozen for later analysis for TNF-α. TNF-α was measured in the faeces using an ELISA method.

Results

All sheep developed acidosis both in the rumen and in the hind-gut, indicating that the acidosis preventing capacity of VM was exceeded. Rumen pH dropped below 5.0 in 4 of the 6 sheep, while faecal pH dropped to below 5.0 in 3 of the 6 sheep. There were no differences in rumen or faecal pH between treatment groups (Table 3). When the sheep were autopsied after 48 hours, the pH along the hind-gut was measured, to estimate a change in pH along the tract towards the faeces from the caecum.

TABLE 3

Average rumen and faecal pH and faecal lactate (36 and 48 hour samples) in sheep overfed grain with or without VM (30 mg/kg).

| | | | | P-values | | |
|---|---|---|---|---|---|---|
| Measurement | Control | VM | SED | Treatment | Time | Treatment × Time |
| Rumen pH | 5.90 | 5.84 | 0.656 | ns | 0.0001 | ns |
| Faecal pH | 7.12 | 7.28 | 0.768 | ns | 0.0001 | ns |
| Faecal L-lactate | 49.6 | 28.2 | | ns | 0.02 | ns |
| Faecal D-lactate | 13.6 | 7.43 | | ns | 0.05 | ns |

The rumen VFA and lactic acid concentrations are shown in Table 4. The VM had a significant effect on the pattern of VFA fermentation. The ratio of Propionate to Acetate+(2× Butyrate) was significantly higher in sheep fed VM. No treatment effects were observed with respect to lactic acid concentration.

TABLE 4

Summary of rumen volatile fatty acid VFA and lactic acid concentrations (mmol/L) proportions (mmol/100 mmol) in sheep fed high grain pellets without any dietary additives, or containing VM (30 mg/kg).

| | | | | P-values | | |
|---|---|---|---|---|---|---|
| Measurement | Control | VM | SED | Treatment | Time | Treatment × Time |
| Total VFA | 82.29 | 81.80 | 23.575 | ns | 0.01 | ns |
| Ac (%) | 62.68 | 50.941 | 9.930 | 0.035 | 0.0001 | ns |
| Pr (%) | 20.46 | 34.36 | 6.365 | 0.005 | 0.001 | 0.006 |
| But (%) | 11.56 | 8.75 | 7.392 | ns | 0.08 | ns |
| L-Lactic acid | 5.11 | 7.33 | | ns | 0.02 | ns |
| D-Lactic acid | 18.04 | 25.12 | | ns | 0.04 | ns |

Faecal TNF-α concentrations are summarised in Table 5. The concentration of TNF-α in the faeces, did increase significantly from time 0 until 48 hours after grain feeding (P=0.019).

TABLE 5

Faecal TNF-α concentrations in 6 sheep overfed a pellet high in Barley and suffering from acute acidosis.

| | | Experimental Hour | | | |
|---|---|---|---|---|---|
| Sheep | Treatment | 0 | 24 | 36 | 48 |
| 1 | Control | 10000 | 12000 | 62000 | 28000 |
| 3 | Control | 20667 | 30000 | 37000 | 40000 |
| 5 | Control | 19333 | 20000 | 51000 | 26000 |
| 2 | VM | 9000 | 12000 | 98333 | 230667 |
| 4 | VM | 16000 | 24000 | 64000 | 66000 |
| 6 | VM | 12000 | 17000 | 25000 | 76000 |
| Averages | Control | 16667 | 20667 | 50000 | 31333 |
| | se | 3355 | 5207 | 7234 | 4372 |
| | VM | 12333 | 17667 | 62444 | 124222 |
| | se | 2028 | 3480 | 21184 | 53300 |
| | Average | 14500 | 19167 | 56222 | 77778 |
| | se | 2003 | 2880 | 10390 | 31677 |

Faecal TNF-α was closely related to faecal pH as measured over the course of the experiment. FIG. 7 shows the change in faecal pH and TNF-α over the course of the experiment. Faecal pH decreased significantly over time (P=0.0001) while faecal TNF-α increased significantly over the same time period (P=0.019). Faecal pH at time 0, 24 and 36 hours was inversely proportional to faecal TNF-α over the time periods 24, 36 and 48 hours.

FIG. 8 illustrates the change in pH of digesta through the gastrointestinal tract to the faeces. It is clear from FIG. 8 that virginiamycin has a consistent effect in reducing acid cumulation (increasing pH) in all parts of the digestive tract, and provides evidence for its use in the prevention and control of acidic gut syndrome in pigs and sheep.

FIG. 8 shows that changes in faecal pH are likely to give a very conservative estimate of the severity of acidic gut syndrome. This observation is also supported by FIG. 6. In both the sheep and pig data, it is clear that the pH in the caecum and proximal colon is very much lower than in the rectum or faeces. It is emphasised that the difference between the faecal/rectal pH and the caecal/proximal colon is nearly one pH unit (10 fold increase). Therefore, what might appear as a relatively minor drop in faecal pH from 7.0 to 6.5 is likely to represent a drop in caecal pH from around 6.8 down to 5.5.

This observation is important for two reasons. Firstly, it means that since faecal pH normally stays high, even when there is hind gut acid accumulation, there has been little evidence of any likely problem. Secondly, when faecal pH falls below 6.5 (which it commonly does—see FIG. 3) there is good evidence that acidic gut syndrome is a potential problem.

A further point made in both FIGS. 6 and 8, is that virginiamycin has a consistent effect in reducing acid accumulation (increasing pH) in all parts of the digestive tract. This provides evidence for its use in the prevention and control of acid gut syndrome. The effect of virginiamycin on pH appears to be less in the faeces than in other parts of the hind gut and it is therefore likely that a prediction of the effects of virginiamycin, assessed by sampling faeces alone will give a conservative estimate of the true benefits associated with reduced acid concentrations.

Discussion

The major finding in this study was the high levels of TNF-α measured in the faeces of sheep with fermentative acidosis in the rumen and hind gut. This is the first time that TNF-α has been studied in animals with fermentative acidosis in the gut and it is the first report of elevated concentrations of TNF-α in response to acid accumulation in the gut. It is a very significant addition to our knowledge of the effects of fermentative acidosis since it was previously considered that the adverse effects of fermentative acidosis were mediated by absorption of acids and systemic acidosis based on the absorbed acid (Blood et al. 1983).

As described by (Rowe, 1997) and (Ding et al., 1998), there is good evidence that lactic acid is not absorbed from the rumen or caecum until there is severe damage to the gut wall. The new disease condition acidic gut syndrome is in fact based on the adverse effects initiated via low pH within the gut causing inflammation of the gut wall and the subsequent release of cytokines which are capable of initiating and exacerbating a wide range of disease conditions well described through their known effects originating from sepsis and other causes of inflammation.

It has been known for some time that the main mediator of endotoxaemia from bacterial infection is through cytokines such as TNF-α (Abbas et al., 1996); (Tracey et al., 1989); (Tracey et al., 1986). This cytokine is prevalent in many conditions including cancer (Balkwill et al., 1987), Cystic Fibrosis (Briars et al., 1995) and HIV infection (Sharpstone et al., 1996). TNF-α is also found in high levels and thought to be one of the main mediators of the effects of irritable bowel disease (IBD) such as Crohn's disease (van Deventer, 1997). Recently, TNF-α levels in faeces of children with active Crohn's disease has been used as a marker of intestinal inflammation and disease severity (Braegger et al., 35 1992); (Nicholls et al., 1993).

TNF-α has also been found to be associated with the degradation of many organs in the body in which basement membranes are affected, including liver abscess (Fukui et al., 1993) and respiratory problems (Tracey et al., 1986).

There are also many secondary effects of TNF-α found in many species including arthritis (Lewthwaite et al., 1995, May, 1997), dermatitis (Nickoloff and Turka, 1993), mastitis and respiratory disease (Godson et al, 1997) that have never previously been related to acid build up in the gut, but are likely to be initiated or exacerbated by TNF-αinduced from acid accumulation in the gut.

The role TNF-α in cachexia or wasting is well established (Tracey et al. 1989; van Deventer, 1997) and it is likely that this is partly due to reduced feed intake. The evidence of TNF-α as a result of acid accumulation indicates the role of cytokines in reduced feed intake observed in Example 6 and offers a new approach to managing the significant industry problem of variable and low feed intake.

Example 8

Faecal pH in mice with ulcerative colitis

Background

TNF is known to be an important mediator of inflammatory bowel disease in humans (vanDeventer, 1997). A model for inducing ulcerative colitis for the study of inflammatory bowel disease involves the addition of a 5% Dextran Sulphate Solution (DSS) to the water of the mice, and within 5 days, the mice show signs of diarrhoea and rectal bleeding associated with ulcerative colitis. Dextran sulphate is considered to be an irritant to the gut wall and no link with acid build up in the gut has been previously suggested. The hypothesis behind this study was that dextran sulphate may in fact provide substrate for rapid fermentation of the hind gut and/or that any irritant effect on the gut wall would increase the rate of flow of digesta, thereby decreasing digestion in the small intestine and increasing hind gut fermentation and acid accumulation.

The aim of this study was to follow changes in faecal pH during the onset and development of inflammatory bowel disease to determine the possible role of hind gut acid accumulation on the development of ulcerative colitis

Materials and Methods

Animals and Housing 25 mice were housed in individual pens over 11 days. They were fed a basal diet common to mice consisting of a commercial mouse pellet. They had water available ad libitum.

On day 1 of the trial 15 mice had sodium dextran sulphate included in their water at 5%. Mice were observed over the next 10 days for incidence of diarrhoea and rectal bleeding as an indication of the onset of acute colitis.

Treatments 10 animals were used for the control group, in which they remained on the basal diet with unlimited $H_2O$ with no additives. 15 mice were used in the colitis group. From day 1 of the trial these mice were fed the basal diet, but with $H_2O$ containing 5% DSS. This DSS addition has been previously found to cause ulcerative colitis in mice when fed for a period of greater than 5 days. These mice remained on this treatment for 10 days.

Measurements and Analysis

Total mouse faecal output was collected daily from all mice, and the samples stored individually in ELISA reaction plates and frozen immediately in liquid nitrogen. Samples were stored at −20° C. for later analysis.

Symptoms of disease were observed and recorded daily for each mouse. Scores from 0 (no symptom) to 5 (severe symptom) were recorded for diarrhoea and rectal bleeding. These were added together to give Total Disease Score for each animal for each day. pH Analysis Individual mouse faecal samples were thawed and diluted with 100 μL of deionised water and mixed until confluent. The pH was then recorded on that sample with an Activon pH probe with Activon pH meter and read to 2 decimal places.

Results

Overall, there was no difference between groups in faecal pH. It is interesting to look at the pH over different periods of the trial however in FIG. 9. The faecal pH in the colitis group declined significantly over the period of days 3 to 7 (P=0.0140), and was significantly lower than the control group over this period (P=0.0426). After day 5 of the experiment however, there were significant signs of colitis with diarrhoea and rectal bleeding both increasing significantly (p=0.0001) as shown in FIG. 10. After this time, the pH of the faeces rose significantly from day 8 to day 10 (P=0.0041), and was significantly higher than the control group (P=0.0265).

There was a strong correlation between average pH and average disease score for the 10 days of the trial ($r^2$=0.74) as seen in FIG. 10.

Discussion

The initial decrease in faecal pH could be indicative of acid build up in the hind gut particularly as FIGS. 6 and 8 show that relatively minor reduction in faecal pH can reflect a much larger reduction in the pH of caecal and colonic digesta. It is however not clear whether hind gut acidosis is a primary or contributory factor in the subsequent development of ulcerative colitis. The main aspect of the discovery reported in this Example is in relation to the pattern of pH change and the similarities with changes seen in response to hind gut acid accumulation shown in FIG. 7.

After the initial decrease in pH before day 5 when the signs of disease were first noted, the pH in the faeces increased significantly from 6.98 on day 6 to 7.58 on day 10 (P=0.0041). The pH in the colitis group was significantly higher than the control group over this period (P=0.0265). There was a strong correlation found between disease score and observed faecal pH ($r^2$=0.3157). It is likely that this rise in faecal pH was probably due to increased blood mucus secretions from the caecum, large intestine and colon in response to damage to the epithelial layers from disease conditions.

There is important information in the similarities observed between this study in mice and the results in ruminants (see FIG. 7). The rise in faecal pH rising after acid build up in the gut is likely to result from increased blood mucus secretions and an increased pH of the faeces could be indicative of damage to the gut. Recognising this apparent anomaly of an increase in faecal pH during the diarrhoea phase of acidic gut syndrome is important new aspect in understanding and recognising the condition of acidic gut syndrome.

When colitis occurs in the mouse, damage to the gut wall leads to a rise in the tissue levels of TNF, and many of the disease symptoms noted in the body as a result of the colitis are mediated through tissue levels of TNF (vanDeventer, 1997). The similarities between patterns of faecal pH change in the mouse in and in sheep with two models (dextran sulphate and grain) causing inflammation in the hindgut provides further evidence of the links between acidic gut syndrome inflammation to the gut wall and the role of inflammatory cytokines exemplified by TNF.

Example 9

Animals or humans with inefficient digestion and absorption of starch and carbohydrate prior to the ileum, may develop chronic acidic gut syndrome which leads to the gradual development of arthritis and sporadic problems of dermatitis. Treatment in accordance with the present invention would initially involve administration of virginiamycin (0.4 mg/kg bodyweight per day) and a change in the dietary regime over the following 2 months in order to stabilise both the arthritis and dermatitis.

Essentially, the change to the dietary regime is designed to minimise the amount of fermentable carbohydrate which passes through the forestomach, stomach and small intestine of said human or animal, and is available for fermentation in the hind gut (ileum, caecum, colon and rectum) of said human or animal.

Typically, the principles on which such a dietary regime may be designed include the following:

1. Exclusion or reduction of grains or starch with characteristics of being resistant to gastric digestion and/or intestinal digestion. For example, high amylase maize, sorghum and ordinary maize.

2. Exclusion or reduction of grains or grain products with high levels of non-starch polysaccharides (particularly soluble non-starch polysaccharides) such as wheat, rye or barley.

3. Ensure that starch-based foods are well cooked to reduce resistance of starch, and ensure it is broken down or gelatinised to make it more readily digestible 4. Reduce consumption of barley, rye, wheat or oat-based fermentation produce, such as beer, which contain more non-starch polysaccharides than similar products produced from rice, maize, sorghum or potatoes.

5. Reduce intake of live yoghurts in combination with carbohydrate sources containing resistant starch and/or non-starch polysaccharide. For example, yoghurt with muesli.

6. Reduce intake of processed starches used as thickeners in food preparation.

7. Avoid a rapid and major change in source and amount of dietary carbohydrate.

8. Avoid large meals, eat slowly and masticate food well.

Example 10

Children with recurring problems of asthma often may enjoy a diet consisting predominantly of wheat-based cereal for breakfast and pasta for other meals, washed down with cordial. Treatment in accordance with the present invention would initially involve administration of virginiamycin to stabilise the condition of acidic gut syndrome. This is accompanied by monitoring of stool pH prior to virginiamycin administration; and for a treatment period of 4 weeks. Changes in dietary habits are difficult to achieve and the introduction of an enzyme mixture by sprinkling (10 g/kg DM of food) over food to assist digestion in the stomach and absorption from the small intestine, would provide an alternative treatment.

Example 11

A busy executive under significant stress at work may have a large breakfast each day of muesli and live Lactobacillus yoghurt. There is often not time for lunch and a large dinner (normally pasta) is quickly consumed on the way to evening activities. The executive finds problems of repeated viral infection (flu and cold sores). Monitoring of faecal pH, endotoxins and TNF reveals higher than normal acidity and detectable levels of TNF and endotoxins. These changes may be reversed over the following three weeks through treatment with virginiamycin. This may act as a stimulus for the executive to change dietary and eating habits and virginiamycin could be withdrawn without recurrence of acidic gut syndrome. A monitoring program (faecal pH and TNF) would be recommended under these conditions.

Industrial Applicability

The present invention makes use of a method for the treatment or prophylaxis of acidic gut syndrome resulting from the accumulation of acid and production of endotoxin in the gastrointestinal tract of a human or an animal, said accumulation resulting from the fermentation of carbohydrate in the gastrointestinal tract of said human or animal, wherein said method comprises administering to said human or animal an effective amount of an active agent capable of preventing or controlling acid and endotoxin accumulation in the gastrointestinal tract.

References

Abbas, A. K., Lichtman, A. H., and Pober, J. S. (1996). "Cellular and molecular Immunology," W. B. Saunders Company, Sydney.

Balkwill, F., Burke, F., Talbot, D., Tavernier, J., Osborne, R., Naylor, S., Durbin, H., and Fiers, W. (1987). Evidence for tumour necrosis factor/cachectin production in cancer. *The Lancet*. ii: 1229–1232.

Beutler, B. A., Milsark, I. W., and Cerami, A. (1985). Cachectin/Tumour Necrosis Factor: Production, distribution and metabolic fate in vivo. *The Journal of Immunology*. 135: 3972–3977.

Blood, D. C., Radostits, O. M. and Henderson, J. A. with contributions by Arundel, J. H. and Gray, C. C. (1983). *Veterinary Medicine* A textbook of diseases of Cattle, Sheep, Pigs, Goats and Horses. pp. 221–227. 69 Ed, Bailliere Tindall, Eastbourne UK.

Braegger, C. P., Nicholls, S., Murch, S. H., Stephens, S., and MacDonald, T. T. (1992). Tumour necrosis factor alpha in stool as a marker of intestinal inflammation. *Lancet (The)* 339: 89–91.

Briars, G. L., Dean, T. P., Murphy, J. L., Rolles, C. J., and Warner, J. O. (1995). Faecal interleukin-8 and tumour necrosis factor-alpha concentrations in cystic fibrosis. *Archives of Diseases in Childhood*. 73: 74–76.

Brown, I. L., and McNaught, K. J. (1997). "The utilisation of high amylose maize starch in animal and human nutrition," University of New England.

Ding, A., Rowe, J. B., Godwin, I. R., Xu, Y., Ball, F. M., and Atkinson, S. (1998). No lactic acid absorbed from the caecum and rumen of sheep. *Australian Journal of Agricultural Research* 49: 293–301.

Dirksen, G. (1970). Acidosis. In "Physiology of Digestion and Metabolism in the Ruminant" (A.T. a.o. Phillipson, ed.), pp. 612–625. Oriel Press, Newcastle upon Tyne.

Dougherty, R. W., Coburn, H. M., and Allison, M. J. (1975). Preliminary study of appearance of endotoxin in circulatory system of sheep and cattle after grain engorgement. *American Journal of Veterinary Research* 36: 831–832.

Dunlop, R. H. (1972). Pathogenesis of ruminal lactic acidosis. *Advances in Veterinary Science and Comparative Medicine* 16: 259–302.

Fikui, H., Kitano, H., Morimura, M., Kikuchi, E., Matsumoto, M., Tsujita, S., Kinoshita, K., Matsumoto, M., Okamoto, Y., and Tsujii, T. (1993). Metabolic fate of endotoxin and blood tumour necrosis factor levels in rats with acute and chronic alcohol loading. *Alcohol and Alcoholism* 28: 65–75.

Garner, H. E., Hutcheson, D. P., Coffman, J. R., Hahn, A. W. and Salem, C. (1987). Lactic Acidosis: a factor associated with equine laminitis. *Journal of Animal Science* 45, 1037–41.

Godson, D. L., baca-Estrada, M. E. and Babuik, L. A. (1997) Applications of Bovine cytokines. pp 2–13 In 'Cytokines in veterinary medicine' (V. E. C. J. Schijns and M. C. Horzinek, Editors). CAB International.

Horovov, D. W., Swiderski, C. E., Robinson, J. A., and Klei, T. R. (1997). "Cytokine production in equine disease," CAB International.

Johnson, K G., Tyrell, J., Rowe, J. B. and Pethick, D. W. (1997). Behavioural changes in stabled horses given non-therapeutic levels of virginiamycin as Founderguard™. *Equine Veterinary Journal* 30:139–143

Kavanagh, N. (1994). Gastric ulcers in pigs. *In Practice* July 1994: 209–213.

Krueger, A. S., Kinden, D. A., Garner. H. E. and Sprouse, R. F. (1986). Ultrastructural study of the equine caecum during onset of laminitis. *American Journal of Veterinary Research* 47, 1804–1812.

Lewthwaite, J., Blake, S., Hardingham, T., Foulkes, R., Stephens, S., Chaplin, L., Emtage, S., Catterall, C., Short, S., and Nesbitt, A. (1995). Role of TNF alpha in the induction of antigen induced arthritis in the rabbit and the anti-arthritic effect of species specific TNF alpha neutralising monoclonal antibodies. *Ann. Rheum. Dis.* 54: 366–374.

May, S. A. (1997) Cytokines in the pathogenesis of equine joint disease. pp 191–199 In 'Cytokines in veterinary medicine' (V. E. C. J. Schijns and M. C. Horzinek, Editors). CAB International.

Nicholls, S., Stephens, S., Braegger, C. P., Walker-Smith, J. A., and MacDonald, T. T. (1993). Cytokines in stools of children with inflammatory bowel disease or infective diarrhoea. *Journal of Clinical Pathology*. 46: 757–760.

Nickoloff, B. J., and Turka, L. A. (1993). Keratinocytes: Key immunocytes of the integument. *American Journal of Pathology* 143: 325–330.

Nocek, J. E. (1997). Bovine acidosis: Implications on laminitis. *Journal of Diary Science* 80: 1005–1028.

Odink, J., Smeets, J. F. M., Visser, I. J. R., Sandman, H., and Snijders, J. M. A. (1990). Hematological and clinico-chemical profiles of healthy swine and swine with inflammatory processes. *Journal of Animal Science* 68: 163–170.

Puppe, B., Tuchscberer, M., and Tuchscherer, A. (1997). The effect of housing conditions and social environment immediately after weaning on the agonistic behaviour, neutrophil/lymphocyte ratio, and plasma glucose level in pigs. *Livestock Production Science* 48: 157–164.

Rowe, J. B., Lees, M. J. and Pethick, D. W. (1994). Prevention of Acidosis and Laminitis Associated with Grain Feeding in Horses. *Journal of Nutrition* 124, 2742S–2744S.

Rowe, J. B. (1997). 'Acidic gut syndrome': is it a problem for animals and humans? In *Recent Advances in Animal Nutrition in Australia*. July 1997: 47–54.

Sharpstone, D. R., Rowbottom, A. W., Nelson, M. R., Lepper, M. W., and Gazzard, B. G. (1996). Faecal Tumour Necrosis Factor-alpha in individuals with HIV-related diarrhoea. *AIDS* 10: 989–994.

Tracey, K. J., Beutler, B., Lowry, S. F., Menyweather, J., Wolpe, S., Milsark, I. W., Hariri, R. J., and Fahe, T. J. (1986). Shock and tissue injury induced by recombinant human cachectin. *Science* 234: 470474.

Tracey, K. J., and Cerami, A. (1993). Tumour Necrosis Factor: An updated review of its biology. *Critical Care Medicine* 21: S415–S422.

Tracey, K. J., Vlassara, H., and Cerami, A. (1989). Cachectin/Tumour necrosis factor. *The Lancet*: 1122–1126.

van Deventer, S. J. H. (1997). Tumour necrosis factor and crohn's disease. *Gut* 40: 443–448.

What is claimed is:

1. A method for the treatment or prophylaxis of acidic gut syndrome resulting from the accumulation of acid and production of endotoxin in the gastrointestinal tract of a human or an animal, said accumulation resulting from the fermentation of carbohydrate in the gastrointestinal tract of said human or animal, wherein said method comprises administering to said human or animal an effective amount of an active agent for immunizing the animal against a microorganism responsible for the fermentation of carbohydrates in the gastrointestinal tract of said human or animal.

2. The method of claim 1, wherein the microorganism is selected from the group consisting of: Aerococcus, Alloiococcus, Carnobacterium, Enterococcus, Lactobacillis, Lactococcus, Leuconostoc, Pediococcu, Streptococcus, and Tetragenacoccus.

3. The method of claim 1, wherein the microorganism is Lactobacillis spp. or *Streptococcus bovis*.

4. The method according to claim 1, wherein said microorganism is *Streptococcus bovis* (Sb-5).

5. The method according to claim 1, wherein the acidic gut syndrome is associated with a condition selected from the group consisting of predisposition to ulceration of the gastrointestinal tract; ulceration of the stomach; immune conditions associated with localized inflammation of the gut; crohn's disease, appendicitis and colitis; reduced feed intake responsible for cachexia and low efficiency in production feeding systems.

6. The method according to claim 1, wherein the acidic gut syndrome is associated with a condition selected from the group consisting of dermatitis; arthritis; rheumatoid arthritis; osteoarthritis; and respiratory tract disorders.

7. The method according to claim 1, wherein the acidic gut syndrome is associated with a condition selected from the group consisting of predisposition to microbial and helminth infections of the gut and infection of the mammary gland.

8. The method according to claim 1, wherein the acidic gut syndrome is associated with a condition selected from the group consisting of immune disorders causing predisposition to infection by bacteria, fungi or protozoa, cystic fibrosis and cancer.

9. The method according to claim 1, wherein the acidic gut syndrome is associated with a condition selected from the group consisting of effects on the pancreas, kidneys, thyroid and other organs of the endocrine system; and homeostasis disorders.

10. The method according to claim 1, wherein the acidic gut syndrome is associated with a condition selected from the group consisting of immune disorders, Alzheimer's disease, impaired reproductive performance; dental caries; viral infections, exacerbation of heat stress; and impaired hair and wool growth.

11. The method according to claim 5, wherein the condition is irritable bowel syndrome.

12. The method according to claim 6, wherein the condition is asthma or predisposition to bleeding in lungs following strenuous exercise.

13. The method according to claim 7, wherein the condition is mastitis.

14. The method according to claim 5, wherein the condition is diabetes, osteoporosis, or hypertension.

15. The method according to claim 10, wherein the condition is multiple sclerosis, amyotrophic lateral sclerosis, chronic fatigue syndrome, myasthenia gravis, or herpes.

* * * * *